United States Patent
Park et al.

(10) Patent No.: US 10,265,261 B2
(45) Date of Patent: Apr. 23, 2019

(54) CLEANSING COMPOSITIONS WITH CONDITIONING PROPERTIES

(71) Applicant: L'OREAL, Paris (FR)

(72) Inventors: Angela Park, Jersey City, NJ (US); Allison Chin, Hoboken, NJ (US); Kamini Patel, Iselin, NJ (US); Heather Lee, Wayne, NJ (US); Jaimie Mecca, Clifton, NJ (US); Ivana Rashid, New York, NY (US)

(73) Assignee: L'OREAL, Paris (FR)

( * ) Notice: Subject to any disclaimer, the term of this patent is extended or adjusted under 35 U.S.C. 154(b) by 155 days.

(21) Appl. No.: 15/339,029

(22) Filed: Oct. 31, 2016

(65) Prior Publication Data

US 2018/0116937 A1     May 3, 2018

(51) Int. Cl.
| | |
|---|---|
| *C11D 1/86* | (2006.01) |
| *A61K 8/60* | (2006.01) |
| *A61Q 5/02* | (2006.01) |
| *A61Q 19/10* | (2006.01) |
| *A61K 8/37* | (2006.01) |
| *A61K 8/42* | (2006.01) |
| *A61K 8/73* | (2006.01) |
| *A61K 8/44* | (2006.01) |
| *A61K 8/46* | (2006.01) |

(52) U.S. Cl.
CPC ............. *A61K 8/602* (2013.01); *A61K 8/375* (2013.01); *A61K 8/42* (2013.01); *A61K 8/44* (2013.01); *A61K 8/466* (2013.01); *A61K 8/73* (2013.01); *A61K 8/737* (2013.01); *A61Q 5/02* (2013.01); *A61Q 19/10* (2013.01); *A61K 2800/30* (2013.01); *A61K 2800/48* (2013.01)

(58) Field of Classification Search
CPC ...................................................... C11D 1/667
USPC ......................................... 510/119, 130, 137
See application file for complete search history.

(56) References Cited

U.S. PATENT DOCUMENTS

| | | |
|---|---|---|
| 4,595,526 A | 6/1986 | Lai |
| 5,318,727 A | 6/1994 | Ohtawa et al. |
| 5,672,576 A | 9/1997 | Behrens et al. |
| 2009/0258807 A1 | 10/2009 | Hoffmann et al. |
| 2010/0197553 A1 | 8/2010 | Barnabas et al. |
| 2010/0197554 A1 | 8/2010 | Koyuncu et al. |
| 2010/0234271 A1* | 9/2010 | Scheuing ................ C11D 1/83 510/465 |
| 2012/0270764 A1 | 10/2012 | Brown et al. |
| 2014/0309154 A1* | 10/2014 | Carter ..................... A61K 8/37 510/119 |
| 2015/0157548 A1 | 6/2015 | De Feij et al. |
| 2016/0022557 A1* | 1/2016 | Galleguillos .......... C11D 3/226 510/123 |
| 2016/0287504 A1* | 10/2016 | Schroeder ............. A61K 8/466 |
| 2018/0071198 A1* | 3/2018 | Lin ......................... A61K 8/85 |

FOREIGN PATENT DOCUMENTS

| | | |
|---|---|---|
| WO | WO-2010/088158 A1 | 8/2010 |
| WO | WO-2010/088162 A1 | 8/2010 |
| WO | WO-2012/015852 A1 | 2/2012 |
| WO | WO-2012/016104 A2 | 2/2012 |
| WO | WO-2014/091111 A2 | 6/2014 |
| WO | WO 2016/184631 A1 | 11/2016 |

OTHER PUBLICATIONS

International Search Report issued and Written Opinion dated Jan. 16, 2018, for corresponding PCT Application No. PCT/US17/57574.
"Kao Chemicals Europe: Emanon HE", Jul. 18, 2016; http://www.kaochemicals:eu.com/products/peg-7-glyceryl-cocoate-0, pp. 1-3, p. 1.

* cited by examiner

*Primary Examiner* — Gregory E Webb
(74) *Attorney, Agent, or Firm* — Polsinelli PC

(57) ABSTRACT

The present disclosure relates to cleansing compositions, which are free of sulfates and ethoxylated surfactants. Methods for making and using the cleansing compositions are also described. The cleansing compositions include: (a) at least 3 wt. % of one or more nonionic surfactant(s) that are not fatty esters; (b) one or more fatty ester(s); (c) one or more non-ethoxylated, sulfate-free anionic surfactant(s); and (d) two or more thickening agents. The cleansing compositions exhibit quality cleansing activity, impart pleasant conditioning benefits, and have a desired viscosity and foam properties.

21 Claims, No Drawings

CLEANSING COMPOSITIONS WITH CONDITIONING PROPERTIES

FIELD OF THE DISCLOSURE

The present disclosure relates to cleansing compositions. The cleansing compositions exhibit quality cleansing activity, impart pleasant conditioning benefits, and have a desired viscosity. Methods for making and using the cleansing compositions are also described.

BACKGROUND

Surfactants are widely used in aqueous based personal care, household, and industrial products. They are typically used as wetting agents, detergents, and emulsifiers. In personal care cleansing products (e.g., shampoos, body washes, facial cleansers, liquid hand soaps, etc.) the surfactant is often the most important component because it provides many of the cleansing attributes of the composition.

Although in principle any surfactant class (e.g., cationic, anionic, nonionic, amphoteric) is suitable in cleansing or cleaning applications, in practice most personal care cleansers and household cleaning products are formulated with anionic surfactants or with a combination of an anionic surfactant as the primary detersive agent with one or more secondary surfactants selected from the other surfactant classes. Anionic surfactants are often used as detersive agents in cleansers and cleaning products because of their excellent cleaning and foaming properties. From the consumer's perspective, the amount and stability of the foam directly relates to the perceived cleaning efficiency of the composition. Generally speaking, the larger the volume of foam produced and the more stable the foam, the more efficient is the perceived cleaning action of the composition. This presents a potential problem in low-surfactant formulations, as foam volume tends to decrease with decreasing surfactant concentration.

Sulfate-based surfactants (such as, for example, sodium lauryl sulfate and sodium lauryl ether sulfate) are particularly popular because of their effectiveness in cleansing, foam production, and stability. Personal care cleansers containing sulfate-based surfactants are also generally easy to thicken with typical thickeners, such as salt and cellulose-based materials. Nonetheless, these particular surfactants can be harsh and irritating to skin. For instance, over-use of sulfate-based surfactants can cause needless drying to the face and scalp, and contribute to color fading and drying of hair. Eliminating sulfate surfactants from cleansing compositions has been challenging because sulfate-free compositions typically have poor foaming properties, are difficult to thicken, and may not provide the desired degree of clarity or transparency. Also, the cleansing ability of sulfate-free composition are often sub-optimal.

SUMMARY OF THE DISCLOSURE

The cleansing compositions of the instant disclosure are free of sulfates and ethoxylated compounds including ethoxylated surfactants, yet exhibit effective/desirable cleansing and foaming properties. Furthermore, the compositions provide a "clean" and refreshing feel, have a pleasant viscosity, and impart moisturizing properties to the hair and/or skin. The stability and viscosity of the compositions allow for the suspension of particulates, such as charcoal powder, that may provide additional desirable benefits to the compositions and/or to the hair (for example, composition structure as well as texture and/or volume to hair).

The cleansing compositions typically include: (a) at least 3 wt. % of one or more nonionic surfactants, which are not fatty esters; (b) one or more fatty esters; (c) one or more non-ethoxylated, sulfate-free anionic surfactants; and (d) two or more thickening agents.

Non-limiting examples of useful nonionic surfactants include fatty alcohols, alkyl(ether)phosphates, alkylpolyglucosides, fatty acid alkanolamides, and mixtures thereof. Non-limiting examples of fatty esters include glycerol fatty esters, sucrose fatty esters, sorbitan fatty esters, and fatty alcohol esters. Non-limiting examples of non-ethoxylated, sulfate-free anionic surfactants include sulfonate surfactants, carboxylic (carboxylate) surfactants, and amino acid surfactants, and mixtures thereof. Non-limiting examples of thickening agents include carboxylic acid polymers, cross-linked polyacrylate polymers, polyacrylamide polymers, polysaccharides, and gums.

The cleansing compositions are typically aqueous compositions. In addition to water, however, the cleansing composition may additionally include water soluble solvents, such as, for example, organic solvents (e.g., glycols, polyols, and lower alcohols).

The cleansing compositions of the instant disclosure may optionally include one or more amphoteric surfactants. Non-limiting examples of amphoteric surfactants include betaines, sultaines, amphoacetates, amphoproprionates, and mixtures thereof.

As one of many possible examples, a cleansing composition according to the instant disclosure may include: (a) about 3 to 25 wt. % one or more nonionic alkypolyglucoside surfactants; (b) about 0.1 to about 5 wt. % of one or more fatty esters, such as glycerol fatty esters and/or sucrose fatty esters; (c) about 0.2 to about 20 wt. % of one or more isethionate surfactants and/or one or more sarcosinate surfactants; (d) about 0.01 to about 5 wt. % of two or more thickening gums; (e) about 50 to 90 wt. % water; and optionally (f) one or more amphoteric surfactants, such as a betaine; wherein all percentages are based on the total weight of the cleansing composition.

The cleansing compositions are particularly useful for cleansing the body, especially the hair and/or skin. Typically, the compositions are applied to the hair and/or skin and subsequently rinsed from the hair and/or skin with water. As mentioned above, the cleansing compositions are mild/gentle and provide conditioning and hydrating properties. Therefore, the compositions may be used in methods for conditioning or hydrating the hair and/skin.

DETAILED DESCRIPTION OF THE DISCLOSURE

The cleansing compositions of the instant disclosure typically include: (a) at least 3 wt. % of one or more nonionic surfactants, which are not fatty esters; (b) one or more fatty esters; (c) one or more non-ethoxylated, sulfate-free anionic surfactants; and (d) two or more thickening agents.

Nonionic surfactants are well known. In some cases, the cleansing compositions include one or more nonionic surfactants selected from the group consisting of one or more fatty alcohols, alkyl(ether)phosphates, alkylpolyglucosides, fatty acid alkanolamides, and mixtures thereof.

Non-limiting examples of fatty alcohols include octyldodecanol, 2-butyloctanol, 2-hexyldecanol, 2-undecylpentadecanol, oleyl alcohol, linoleyl alcohol, isostearyl alcohol, undecylenyl alcohol, linolenyl alcohol, myristyl alcohol, cetyl alcohol, stearyl alcohol, cetearyl alcohol (mixture of cetyl alcohol and stearyl alcohol), octyldodecanol, 2-butyloctanol, 2-hexyldecanol, 2-undecylpentadecanol, oleic alcohol, linoleic alcohol, behenyl alcohol, and mixtures thereof.

Non-limiting examples of alkyl(ether)phosphates include Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate, and mixtures thereof.

Non-limiting examples of alkylpolyglucosides include decyl glucoside, stearyl glucoside, lauryl glucoside, coco-glucoside, cetearyl glucoside, decyl lauryl glucoside, and mixtures thereof.

Non-limiting examples of alkanolamides include oleic acid diethanolamide, oleic acid monoisopropanolamide, myristic acid monoethanolamide, soya fatty acids diethanolamide, stearic acid ethanolamide, linoleic acid diethanolamide, behenic acid monoethanolamide, isostearic acid monoisopropanolamide, erucic acid diethanolamide, ricinoleic acid monoethanolamide, coconut isopropanolamide (INCI name: Cocamide MIPA), coconut fatty acid monoethanolamide (INCI name: Cocamide MEA), coconut fatty acid diethanolamide, palm kernel fatty acid diethanolamide, lauric monoethanolamide, lauric diethanolamide, lauric isopropanolamide polyoxyethylene coconut fatty acid monoethanolamide, and mixtures thereof.

In some cases, the cleansing compositions include one or more alkylpolyglucosides. For example, the one or more alkylpolyglucosides may include decyl glucoside, stearyl glucoside, lauryl glucoside, coco-glucoside, cetearyl glucoside, decyl lauryl glucoside, and mixtures thereof. In some instances, decyl glucoside is included in the cleansing compositions.

The total amount of the one or more nonionic surfactants is typically about 3 wt. % to about 25 wt. %, based on the total weight of the cleansing composition. In some cases, the total amount of the one or more nonionic surfactants is about 3 wt. % to about 20 wt. %, about 3 wt. % to about 18 wt. %, about 3 wt. % to about 16 wt. %, about 3 wt. % to about 15 wt. %, about 4 wt. % to about 25 wt. %, about 4 wt. % to about 20 wt. %, about 4 wt. % to about 18 wt. %, about 4 wt. % to about 16 wt. %, about 4 wt. % to about 15 wt. %, about 5 wt. % to about 25 wt. %, about 5 wt. % to about 20 wt. %, about 5 wt. % to about 18 wt. %, about 5 wt. % to about 16 wt. %, about 5 wt. % to about 15 wt. %, greater than 5 wt. % to about 25 wt. %, greater than 5 wt. % to about 20 wt. %, greater than 5 wt. % to about 18 wt. %, greater than 5 wt. % to about 16 wt. %, greater than 5 wt. % to about 15 wt. %.

Various types of fatty esters are known and can be used in the cleansing compositions. For example, in some cases, the fatty esters may be glycerol (also called "glyceryl") fatty esters, sucrose fatty esters, sorbitan fatty ester, fatty alcohol esters, or mixtures thereof. In some cases, the cleansing compositions include two or more fatty esters; for example, one or more glycerol fatty esters and one or more sucrose fatty esters (e.g., glyceryl oleate and sucrose cocoate). Additional non-limiting examples of fatty esters that may be used include fatty alcohol esters such as esters of $C_{6-22}$ fatty acids with a monohydric alcohol and/or esters of $C_{6-22}$ fatty alcohols with a monocarboxylic acid. More specific non-limiting examples include isopropyl isostearate, n-propyl myristate, isopropyl myristate, hexyl laurate, hexadecyl isostearate, hexyldecyl laurate, hexyldecyl octanoate, n-propyl palmitate, isopropyl palmitate, and mixtures thereof.

The total amount of the one or more fatty esters is typically about 0.1 wt. % to about 5 wt. %, based on the total weight of the cleansing composition. In some cases, the total amount of the one or more fatty esters may be about 0.1 wt. % to about 4 wt. %, about 0.1 wt. % to about 3 wt. %, about 0.2 wt. % to about 5 wt. %, about 0.2 wt. % to about 4 wt. %, about 0.2 wt. % to about 3 wt. %, about 0.5 wt. % to about 5 wt. %, about 0.5 wt. % to about 4 wt. %, about 0.5 wt. % to about 3 wt. %, about 1 wt. % to about 5 wt. %, about 1 wt. % to about 4 wt. %, or about 1 wt. % to about 3 wt. %.

The cleansing compositions typically include one or more non-ethoxylated, sulfate-free anionic surfactants. Non-limiting examples of non-ethoxylated, sulfate-free anionic surfactants include sulfonate surfactants, carboxylic (carboxylate) surfactants, amino acid surfactants, and mixtures thereof. In some cases, the cleansing compositions include one or more sulfonate surfactants. Non-limiting examples of sulfonate surfactants include isethionate surfactants, sulfosuccinate surfactants, sulfoacetate surfactants, and mixtures thereof. Non-limiting examples of isethionate surfactants include sodium cocoyl isethionate, sodium lauroyl isethionate, sodium oleoyl isethionate, sodium oleoyl methyl isethionate, sodium lauroyl methyl isethionate, sodium stearoyl isethionate, sodium stearoyl methyl isethionate, ammonium cocoyl isethionate, and mixtures thereof. An example of a sulfosuccinate surfactant is sodium dioctyl sulfosuccinate. An example of a sulfoacetate surfactant is sodium lauryl sulfoacetate.

In some cases, one or more isethionate surfactants may be used, for example, in a total amount of about 0.1 wt. % to about 15 wt. %, based on the total amount of the cleansing composition. In some instances, the total amount of the one or more isethionate surfactants is about 0.1 to about 12 wt. %, about 0.1 to about 10 wt. %, about 0.1 to about 8 wt. %, about 0.1 to about 6 wt. %, about 0.1 to about 5 wt. %, about 0.5 to about 15 wt. %, about 0.5 to about 12 wt. %, about 0.5 to about 10 wt. %, about 0.5 wt. % to about 8 wt. %, about 0.5 to about 6 wt. %, about 0.5 wt. % to about 5 wt. %, about 1 wt. % to about 15 wt. %, about 1 wt. % to about 12 wt. %, about 1 wt. % to about 10 wt. %, about 1 wt. % to about 8 wt. %, about 1 wt. % to about 6 wt. %, about 1 wt. % to about 5 wt. %, about 1 wt. % to about 4 wt. %, or about 1 wt. %, about 3 wt. %.

In some cases, one or more amino acid surfactants may be included in the cleansing compositions, for example, in a total amount of about 0.1 wt. % to about 15 wt. %. Non-limiting examples of amino acid surfactants include taurates, alanine or alaninate surfactants, sarcosinate surfactants, aspartate surfactants, and mixtures thereof. In some cases, one or more sarcosinate surfactants is included. Non-limiting examples of sarcosinate surfactants include potassium lauroyl sarcosinate, potassium cocoyl sarcosinate, sodium cocoyl sarcosinate, sodium lauroyl sarcosinate, sodium myristoyl sarcosinate, sodium palmitoyl sarcosinate, and mixtures thereof.

When one or more sarcosinate surfactants are included in the cleansing compositions, the total amount of the one or more sarcosinate surfactants is typically about 0.1 wt. % to about 15 wt. %, based on the total weight of the cleansing composition. IN some cases, the total amount of the one or more sarcosinate surfactants is about 0.1 to about 12 wt. %, about 0.1 to about 10 wt. %, about 0.1 to about 8 wt. %, about 0.1 to about 6 wt. %, about 0.5 wt. % to about 15 wt. %, about 0.5 wt. % to about 12 wt. %, about 0.5 % to about 10 wt. %, about 0.5 wt. % to about 8 wt. %, about 0.5 wt. % to about 6 wt. %, about 1 wt. % to about 15 wt. %, about 1 wt. % to about 12 wt. %, about 1 wt. % to about 10 wt. %, about 1 wt. % to about 8 wt. %, about 1 wt. % to about 6 wt. %, about 2 wt. % to about 10 wt. %, about 2 wt. % to about 8 wt. %, or about 2 wt. % to about 6 wt. %.

In some instances, the cleansing compositions include two or more non-ethoxylated, sulfate-free anionic surfactants. For examples, the cleansing compositions may include one or more isethionate surfactants and one or more amino acid surfactants (e.g., one or more sarcosinate surfactant). Regardless of whether the cleansing composition includes one, two, three, or more non-ethoxylated, sulfate-free anionic surfactants, the total amount of the non-ethoxylated, sulfate-free anionic surfactants in the cleansing compositions is typically about 1 wt. % to about 20 wt. %, based on the total weight of the cleansing composition. In some cases, the total amount of the non-ethoxylated, sulfate-free anionic surfactants may be about 1 wt. % to about 15 wt. %, about 1 wt. % to about 12 wt. %, about 1 wt. % to about 10 wt. %, about 2 wt. % to about 20 wt. %, about 2 wt. % to about 15 wt. %, about 2 wt. % to about 12 wt. %, or about 2 wt. % to about 10 wt. %.

Two or more thickening agents are typically included in the cleansing compositions. Thickening agents are sometimes referred to as rheology modifiers or viscosity modifiers. Non-limiting examples of thickening agents that may be used include carboxylic acid polymers, crosslinked polyacrylate polymers, polyacrylamide polymers, polysaccharides, and gums. In some instances, one or more gums are included. Non-limiting examples of gums include acacia, agar, algin, alginic acid, ammonium alginate, amylopectin, calcium alginate, calcium carrageenan, carrageenan, dextrin, gelatin, gellan gum, guar gum, hydroxypropyl guar, guar hydroxypropyltrimonium chloride, hydroxypropyl guar hydroxypropyltrimonium chloride, karaya gum, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof. In some cases, the cleansing compositions include two or more gums selected from the group consisting of sclerotium gum, gellan gum, hydroxypropyl guar hydroxypropyltrimonium chloride, and mixtures thereof.

In some other cases, the two or more gums in the cleansing compositions comprise hydroxypropyl guar hydroxypropyltrimonium chloride and one or more gums selected from the group consisting of acacia, agar, algin, alginic acid, ammonium alginate, amylopectin, calcium alginate, calcium carrageenan, carrageenan, dextrin, gelatin, gellan gum, guar gum, hydroxypropyl guar, guar hydroxypropyltrimonium chloride, karaya gum, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof. In yet some other cases, the two or more gums in the cleansing compositions comprise hydroxypropyl guar hydroxypropyltrimonium chloride and one or more gums selected from the group consisting of gellan gum, sclerotium gum, and mixtures thereof.

The total amount of the two or more thickening agents is typically about 0.01 to about 5 wt. %, based on the total weight of the cleansing composition. In some cases, the total amount of the one or more thickening agents is about 0.01 to about 4 wt. %, about 0.01 wt. % to about 3 wt. %, about 0.01 wt. % to about 2 wt. %, about 0.1 to about 5 wt. %, about 0.1 to about 4 wt. %, about 0.1 to about 3 wt. %, about 0.1 to about 2 wt. %, about 0.5 wt. % to about 5 wt. %, about 0.5 to about 4 wt. %, about 0.5 wt. % to about 3 wt. %, about 0.5 wt. % to about 2 wt. %.

In some cases, when hydroxypropyl guar hydroxypropyltrimonium chloride comprises the two or more thickening agents, it is present in the compositions of the present invention in an amount of from about 0.01 to about 4 wt. %, based on the total weight of the cleansing composition. In some cases, the total amount of hydroxypropyl guar hydroxypropyltrimonium chloride is about 0.01 to about 3 wt. %, about 0.01 wt. % to about 2 wt. %, about 0.01 wt. % to about 1 wt. %, or about 0.1 wt. %, about 0.2 wt. %, about 0.3 wt. %, about 0.4 wt. %, about 0.5 wt. %, about 0.6 wt. %, about 0.7 wt. %, about 0.8 wt. %, about 0.9 wt. %, about 1 wt. %.

In some cases, the cleansing compositions are free (or essentially free) of xanthan gum and/or xanthan gum derivatives. In some cases, the cleansing composition may include less than about 0.5 wt. %, less than about 0.1 wt. %, less than about 0.05 wt. %, less than about 0.01 wt. %, or no xanthan gum, based on the total weight of the cleansing composition.

Typically, the viscosity of the cleansing compositions is from about 65 to about 120 seconds. Viscosity is measured by determining the number of seconds it takes to collect 90 g of test-material (cleansing composition) from a constant height (19.2 cm) at 25° C. using a Ford Viscosity Cup #6, through a constant area, $9\pi$ mm$^2$.

The cleansing compositions are typically aqueous compositions comprising at least 50 wt. % of water, or at least 50 wt. % of a mixture of water and one or more water soluble or substantially water soluble solvents. As used herein, the term "substantially water soluble" means that the organic solvent has a solubility of more than 50% in water at 20° C. Non-limiting examples of water soluble solvents include organic solvents (e.g., glycols, polyols, and lower alcohols).

The cleansing compositions may optionally include one or more amphoteric surfactants, for example, betaines, sultaines, amphoacetates, amphoprionates, and mixtures thereof. In some cases, one or more betaines are included. Non-limiting examples of amphoteric surfactants include (C8-C20)alkylbetaines, (C8-C20)alkylamido (C1-C6)alkylbetaines, sulfobetaines, (C8-C20)alkylsulfobetaines, (C8-C20)alkylamido(C1-C6)alkylsulfobetaines, (C8-C20)alkylamphoacetate, (C8-C20)alkylamphodiacetate, and their salts. Mention may be made of, for example, coco-betaine, cocamidopropylbetaine, sodium cocoamphoacetate, and disodium cocoamphodiacetate.

The total amount of the one or more amphoteric surfactants, when present, is typically about 0.1 wt. % to about 10 wt. %, based on the total weight of cleansing composition. In some cases, the total amount of the one or more amphoteric surfactants is about 0.1 wt. % to about 8 wt. %, 0.1 wt. % to about 6 wt. %, 0.1 wt. % to about 5 wt. %, about 0.1 wt. % to about 4 wt. %, 0.5 wt. % to about 10 wt. %, 0.5 wt. % to about 8 wt. % about 0.5 wt. % to about 6 wt. %, about 0.5 to about 5 wt. %, about 0.5 wt. % to about 4 wt. %, about 1 wt. % to about 10 wt. %, about 1 wt. % to about 8 wt. %, about 1 wt. % to about 6 wt. %, about 1 wt. % to about 5 wt. %, or about 1 wt. % to about 4 wt. %.

The cleansing compositions may be personal cleansing compositions, such as personal rinse-off cleansing compositions. These include, for example, a body wash, a shower gel, liquid hand soap, a shampoo, a conditioner, a facial cleanser, and the like. In some cases, the cleansing composition is a shampoo. In some cases, the shampoo is a conditioning and hydrating shampoo.

As mentioned previously, the cleansing compositions are typically free (or essentially free) of sulfates and ethoxylated compounds including surfactants, such as, for example sodium laureth sulfate, sodium lauryl sulfate, laureths, pareths, etc. Furthermore, in some cases, the cleansing compositions are free (or essentially free) of alkoxylated compounds including alkoxylated surfactants.

In some cases, the hair care compositions typically include less than about 2 wt. %, about 1 wt. %, about 0.5 wt. %, or about 0.1 wt. % of sulfates and ethoxylated surfactants. Furthermore, the compositions may optionally be free (or essentially free) of free of silicone (including silicone oils). In some cases, the cleansing compositions may include less than about 5 wt. %, about 4 wt. %, about 3 wt. %, about 2 wt. %, about 1 wt. %, about 0.5 wt. %, or about 0.1 wt. % or less of silicone (including silicone oils).

The cleansing compositions are particularly useful in methods for cleansing the body, especially the hair and/or skin, and particularly the hair of the head or the skin of the face. These methods comprise applying a composition disclosed herein to the body, hair, skin, and/or face, and optionally rinsing off the cleansing composition (usually with water) or wiping-away the composition. The compositions may be used in methods for gently hydrating the hair and/or skin, wherein the methods comprise application of the cleansing composition to hair and/or skin.

More exhaustive but non-limiting lists of components useful in the cleansing compositions disclosed herein are provided below.

Nonionic Surfactants

Examples of nonionic surfactants include fatty alcohols, alkyl(ether)phosphates, alkylpolyglucosides, fatty acid alkanolamides, and mixtures thereof.

Fatty Alcohols

The fatty alcohols correspond to linear, branched saturated/unsaturated fatty alcohols comprising from 6 to 60 carbon atoms and preferably correspond to the formula R—OH in which R is a saturated or unsaturated, linear or branched hydrocarbon-based radical, comprising 6 to 60 carbon atoms, or from 10 to 50 carbon atoms, or from 12 to 24 carbon atoms, or from 10 to 22 carbon atoms, optionally comprising one or more OH groups.

The saturated fatty alcohols may be branched and can be in liquid form. They can optionally comprise, in their structure, at least one aromatic or non-aromatic ring.

The unsaturated fatty alcohols have in their structure at least one double or triple bond but usually one or more double bonds. When several double bonds are present, there are often 2 or 3 of them and they can be conjugated or unconjugated. These unsaturated fatty alcohols can be linear or branched. They can optionally comprise, in their structure, at least one aromatic or non-aromatic ring.

Liquid fatty alcohols may be selected, for example, from octyldodecanol, 2-butyloctanol, 2-hexyldecanol, 2-undecylpentadecanol, oleyl alcohol, linoleyl alcohol, isostearyl alcohol, undecylenyl alcohol, linolenyl alcohol and mixtures thereof.

The fatty alcohols may be in solid form and may be non-oxyalkylenated and/or non-glycerolated. These fatty alcohols may be constituents of animal or plant waxes.

The solid fatty alcohol may represent a mixture of fatty alcohols, which means that several species of fatty alcohol may coexist, in the form of a mixture, in a commercial product. One example of such a commercial product is cetearyl alcohol, a mixture of cetyl alcohol and stearyl alcohol, commercially available under the trade name of LANETTE-O from the company BASF. Cetyl alcohol may also be commercially available under the tradename of LANETTE 16 from the company BASF.

In some cases, a solid fatty alcohols may be myristyl alcohol, cetyl alcohol, stearyl alcohol, cetearyl alcohol, octyldodecanol, 2-butyloctanol, 2-hexyldecanol, 2-undecylpentadecanol, oleic alcohol, linoleic alcohol, behenyl alcohol, or a mixture thereof.

Other suitable examples of solid fatty alcohols include branched solid fatty alcohols chosen from 2-dodecylhexadecanol, 2-tetradecyl-1-octadecanol, 2-tetradecyl-1-eicosanol, 2-hexadecyl-1-octadecanol and 2-hexadecyl-1-eicosanol, and mixtures thereof.

In some cases, the fatty alcohol may be cetyl alcohol, stearyl alcohol, or cetearyl alcohol. Accordingly, the fatty alcohol may be selected from the group consisting of cetyl alcohol, stearyl alcohol, cetearyl alcohol, and mixtures thereof.

Alkyl(ether)phosphates

Suitable alkyl(ether)phosphates include, but are not limited to, alkoxylated alkyl phosphate esters and alkyl phosphate esters corresponding to a mono-ester of formula (I) and salts thereof:

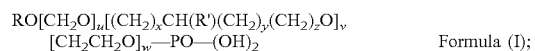

a di-ester corresponding to formula (II) and salts thereof:

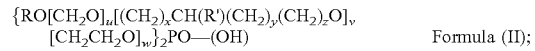

a tri-ester corresponding to formula (III):

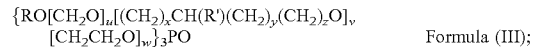

and combinations thereof, wherein:

R is a hydrocarbon radical containing from 6 to 40 carbon atoms;

u, v and w, independently of one another, represent numbers of from 0 to 60;

x, y and z, independently of one another, represent numbers of from 0 to 13;

R' represents hydrogen, alkyl, the sum of x+y+z being ≥0. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formulas (I), (II) and (III), R is linear or branched, acyclic or cyclic, saturated or unsaturated, aliphatic or aromatic, substituted or unsubstituted, preferably a linear or branched, acyclic $C_{6-40}$ alkyl or alkenyl group or a $C_{1-40}$ alkyl phenyl group, more particularly a $C_{8-22}$ alkyl or alkenyl group or a $C_{4-18}$ alkyl phenyl group, more preferably a $C_{12-18}$ alkyl group or alkenyl group or a $C_{6-16}$ alkyl phenyl group; u, v, w, independently of one another, is preferably a number from 2 to 20, more preferably a number from 3 to 17 and most preferably a number from 5 to 15;

x, y, z, independently of one another, is preferably a number from 2 to 13, more preferably a number from 1 to 10 and most preferably a number from 0 to 8.

In general, the lower the number of carbon atoms in the R group of the phosphate esters, the more irritating to the skin and the less soluble in water the phosphate ester becomes. In contrast, the higher the number of carbon atoms in the R group, the milder to the skin and the thicker and waxy the resultant product becomes. Accordingly, in some cases, R has from 12 to 18 carbon atoms.

In some cases, the alkyl phosphate esters are Cetyl phosphate (Hostaphat CC 100), Stearyl phosphate (Hostaphat CS 120) from Clariant.

In some instances, the alkyl(ether)phosphates are chosen from Oleth-3 phosphate, Oleth-10 phosphate, Ceteth-10 phosphate, a mixture of Ceteth-10 phosphate and Dicetyl phosphate, Dicetyl phosphate, Cetyl phosphate, Stearyl phosphate, and mixtures thereof.

Alkylpolyglucosides

The alkyl(poly)glucoside (alkylpolyglycoside) is represented especially by the following general formula:

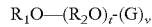

$R_1O—(R_2O)_t-(G)_v$ wherein:
$R_1$ represents a linear or branched alkyl or alkenyl radical comprising 6 to 24 carbon atoms and especially 8 to 18 carbon atoms, or an alkylphenyl radical whose linear or branched alkyl radical comprises 6 to 24 carbon atoms and especially 8 to 18 carbon atoms;
$R_2$ represents an alkylene radical comprising 2 to 4 carbon atoms,
G represents a sugar unit comprising 5 to 6 carbon atoms,
t denotes a value ranging from 0 to 10 and preferably 0 to 4,
v denotes a value ranging from 1 to 15 and preferably 1 to 4.

In some cases, the alkylpolyglycoside surfactants are compounds of the formula described above in which:
$R_1$ denotes a linear or branched, saturated or unsaturated alkyl radical comprising from 8 to 18 carbon atoms,
$R_2$ represents an alkylene radical comprising 2 to 4 carbon atoms,
t denotes a value ranging from 0 to 3 and preferably equal to 0,
G denotes glucose, fructose or galactose, preferably glucose;
the degree of polymerization, i.e. the value of v, possibly ranging from 1 to 15 or from 1 to 4; the mean degree of polymerization more particularly being between 1 and 2.

The glucoside bonds between the sugar units are generally of 1-6 or 1-4 type and preferably of 1-4 type. In some cases, the alkyl(poly)glycoside surfactant is an alkyl(poly)glucoside surfactant. C8/C16 alkyl(poly)glycosides 1,4, and especially decyl glucosides and caprylyl/capryl glucosides are also useful.

Among the commercial products, mention may be made of the products sold by the company COGNIS under the names PLANTAREN® (600 CS/U, 1200 and 2000) or PLANTACARE® (818, 1200 and 2000); the products sold by the company SEPPIC under the names ORAMIX CG 110 and ORAMIX NS 10; the products sold by the company BASF under the name LUTENSOL GD 70, or else the products sold by the company CHEM Y under the name AG10 LK.

In some cases, use is made of C8/C16-alkyl(poly)glucosides 1,4, especially as an aqueous 53% solution, such as those sold by COGNIS under the reference Plantacare® 818 UP.

In some cases, the alkylpolyglucoside is chosen from decyl glucoside, stearyl glucoside, lauryl glucoside, coco-glucoside, cetearyl glucoside, decyl lauryl glucoside, and mixtures thereof.

Fatty Acid Alkanolamides

Suitable fatty acid alkanolamides include those formed by reacting an alkanolamine and a C6-C36 fatty acid. Such surfactants can be chosen from mono-alkanolamides and di-alkanolamides of C6-C36 fatty acids, and preferably from mono-alkanolamides and di-alkanolamides of C8-C30 fatty acids or of C8-C24 fatty acids, and may have a C2-3 hydroxyalkyl group. Examples thereof include, but are not limited to: oleic acid diethanolamide, oleic acid monoisopropanolamide, myristic acid monoethanolamide, soya fatty acids diethanolamide, stearic acid ethanolamide, linoleic acid diethanolamide, behenic acid monoethanolamide, isostearic acid monoisopropanolamide, erucic acid diethanolamide, ricinoleic acid monoethanolamide, coconut isopropanolamide (INCI name: Cocamide MIPA), coconut fatty acid monoethanolamide (INCI name: Cocamide MEA), coconut fatty acid diethanolamide, palm kernel fatty acid diethanolamide, lauric monoethanolamide, lauric diethanolamide, lauric isopropanolamide polyoxyethylene coconut fatty acid monoethanolamide, and mixtures thereof.

In some cases, the fatty acid alkanolamide is chosen from Cocamide MIPA, Cocamide MEA (Coco monoethanolamide), and mixtures thereof.

In some cases, the at least one nonionic surfactant is selected from cetyl alcohol, stearyl alcohol, cetearyl alcohol (mixture of cetyl alcohol and stearyl alcohol), octyldodecanol, isostearyl alcohol, 2-hexyl decanol, palmityl alcohol, myristyl alcohol, stearyl alcohol, lauryl alcohol, oleic alcohol (or oleyl), linoleyl alcohol (or linoley-ether), linolenic alcohol (or linolenyl) and undecylenic alcohol, and mixtures thereof, and more preferably from cetyl alcohol, stearyl alcohol, and cetearyl alcohol, Dicetyl phosphate, Dicetyl phosphate, Cetyl phosphate, Stearyl phosphate, decyl glucoside, cetearyl glucoside, decyl lauryl glucoside, stearyl glucoside, coco-glucoside, cocamide MIPA, and mixtures thereof.

Fatty Esters

The fatty esters of the present invention may be chosen from glycerol (also called "glyceryl") fatty esters, sucrose fatty esters (also known as "sucrose fatty acid esters"), sorbitan fatty ester, fatty alcohol esters, or mixtures thereof. The fatty esters in the compositions of the present invention may also be referred to as nonionic co-emulsifiers.

The glyceryl esters that may be included in the cleansing compositions include, but are not limited to, glyceryl monoesters, such as glyceryl monoesters of C16-C22 saturated, unsaturated and branched chain fatty acids such as glyceryl oleate, glyceryl monostearate, glyceryl monoisostearate, glyceryl monopalmitate, glyceryl monobehenate, and mixtures thereof. For examples, the glyceryl ester may be chosen from glyceryl oleate, glyceryl monostearate (glyceryl stearate), glyceryl monoisostearate, glyceryl monopalmitate, glyceryl monobehenate, and mixtures thereof. In one embodiment, the glyceryl ester is glyceryl oleate.

Non-limiting examples of glycerol fatty esters that may be used include: glyceryl caprate, glyceryl caprylate, glyceryl oleate, glyceryl linoleate, glyceryl myristate, glyceryl capromyristate, glyceryl stearate, glyceryl hydroxy stearate, glyceryl isostearate, glyceryl ricinoleate, glyceryl dilaurate, glyceryl dioleate, glyceryldistearate, glycerylmono/dicaprylate, glycerylmono/dimyristate, glycerylstearatepalmitate, glyceryltricaprate/caprylate, caprylic/capricdiglycerylsuccinate, caprylic/capric glycerides, caprylic/capric/isostearic/adipictriglycerides, caprylic/capric/linoleictriglycerides, caprylic/caprictriglycerides, caprylic/capric/stearictriglycerides, glyceryltrilaurate/stearate, glyceryldi/tripalmitostearate, glyceryldi/tritristearate, caprylictriglyceride, caprylic/capric/laurictriglycerides, glyceryltriheptanoate, glyceryl trioctanoate, glyceryl trilaurate, glyceryl trioleate, glyceryltristearate, glyceryltris-12-hydroxystearate, glyceryltriacetyl hydroxystearate, glyceryl triacetyl ricinioleate, glyceryl triisostearate, glyceryl tribehenate, and mixtures thereof.

The fatty acid in the sucrose fatty acid ester can be any fatty acid, and can contain between 4 and 28 carbon atoms, typically between 8 and 28 carbon atoms, and typically between 8 and 25 carbon atoms, such as between 8 and 18 carbon atoms, such as 8, 9, 10, 11, 12, 13, 14, 15, 16, 17 and 18 carbon atoms. The fatty acid can be synthetic or naturally occurring, and include linear and branched fatty acids. The fatty acids include, but are not limited to, myristic acid, palmitic acid, stearic acid, oleic acid, caproic acid, capric acid, myristic acid, decanoic acid and pelargonic acid.

Thus, the sucrose fatty acid ester includes sucrose monoesters, diesters, triesters and polyesters, and mixtures thereof, and typically contain sucrose monoesters. The sucrose fatty acid esters includes single fatty acid esters and also include homogeneous mixtures of sucrose esters, containing members with different lengths of fatty acid carbon chain and/or members with different degrees of esterification. For example, the sucrose fatty acid esters include mixtures of monoesters, diesters, triesters, and/or polyesters.

Sucrose fatty acid esters are compounds having the following formula shown in Scheme I below.

Scheme I

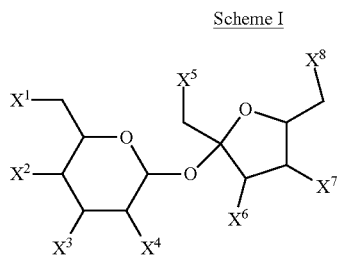

where each of $X^1$, $X^2$, $X^3$, $X^4$, $X^5$, $X^6$, $X^7$ and $X^8$ independently is:

a hydroxyl (—OH) group, or

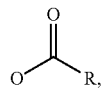

where:
each R is an alkyl group having 3-27 carbon atoms; and
when more than one of $X^1$, $X^2$, $X^3$, $X^4$, $X^5$, $X^s$, $X^7$ and $X^8$ is

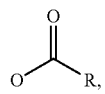

each R can be a different alkyl group (e.g., having different number of carbon atoms and/or different saturation), or can be the same alkyl group.

Typically, in the sucrose fatty acid ester, each R has between 7 and 27 carbon atoms, and typically between 7 and 19 atoms, such as 7, 8, 9, 10, 11, 12, 13, 14, 15, 16, 17, 18, or 19 carbon atoms or between 7 and 17 carbon atoms.

An alkyl group can be a straight chain or branched alkyl group, can be substituted or unsubstituted, and can be a "saturated alkyl group," meaning that it does not contain any alkene or alkyne groups; or an "unsaturated alkyl group," meaning that it contains at least one alkene or alkyne group. An alkyl group that includes at least one carbon-carbon double bond (C═C) also is referred to by the term "alkenyl," and alkenyl groups optionally can be substituted. An alkyl group that includes at least one carbon-carbon triple bond (C≡C) also is referred to by the term "alkynyl," and alkynyl groups optionally can be substituted.

An exemplary monoester has the following structure:

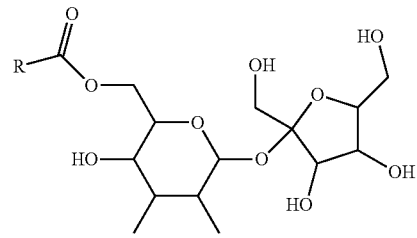

where R is an alkyl group having 3-27 carbons, and typically 7-27 carbons. The sucrose fatty acid esters include blends of sucrose fatty acid esters, which typically include monoesters, and can also include diesters, triesters and polyesters, which have structures according to Scheme V, above, where two (diesters), three (triesters) or more (polyesters) of $X^1$, $X^2$, $X^3$, $X^4$, $X^5$, $X^6$, $X^7$ and $X^8$, (and typically $X^1$ and $X^8$) independently, are

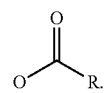

The sucrose fatty acid esters include sucrose fatty ester blends, for example, sucrose ester mixtures containing a specified amount (e.g., percent, by weight) of sucrose monoesters. Exemplary surfactants include sucrose ester mixtures having at least at or about 50%, by weight (w/w), monoester, such as at or about or at least at or about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%, by weight (w/w), sucrose monoesters, and typically at least at or about 60%, by weight or at least at or about 70%, by weight (w/w), monoesters. The surfactants include mixtures of sucrose esters containing at least at or about 50% sucrose monoesters, mixtures of sucrose esters containing at least at or about 60% sucrose monoesters, mixtures of sucrose esters containing at least at or about 70% sucrose monoesters, mixtures of sucrose esters containing at least at or about 80% sucrose monoesters, and mixtures of sucrose esters containing at least at or about 90% sucrose monoesters, for example, mixtures containing at or about 72% sucrose monoesters, at or about 61% sucrose monoesters, or at or about 90% sucrose monoesters.

The sucrose fatty acid esters include sucrose fatty acid monoesters, such as sucrose monocaprylate, sucrose monodecanoate, sucrose monolaurate, sucrose monomyristate, sucrose monopalmitate, sucrose monostearate, sucrose monopelargonate, sucrose monoundecanoate, sucrose monotridecanoate, sucrose monopentadecanoate and sucrose monoheptadecanoate. The sucrose fatty acid esters further include mixtures containing varying percentages of monoesters, diesters, triesters and polyesters, such as, but not limited to, a mixture having at or about 72% monoesters, 23% diesters, 5% triesters and 0% polyesters; a mixture having at or about 61% monoesters, 30% diesters, 7% triesters, and 2% polyesters; and a mixtures having at or about 52% monoesters, 36% diesters, 10% triesters and 2% polyesters.

Examples of sucrose fatty acid esters that may be used include sucrose cocoate sucrose laurate (and) aqua (and) alcohol (Surfhope(R) C-1215 commercially available from Mitsubishi-Kagaku), sucrose laurate, sucrose myristate, sucrose palmitate, sucrose polystearate, sucrose tristearate, sucrose distearate, sucrose stearate, sucrose dilaurate, sucrose hexaerucate, sucrose oleate, sucrose pentaerucate, sucrose polybehenate, sucrose polycottonseedate, sucrose polylaurate, sucrose polylinoleate, sucrose polypalmate, sucrose polyoleate, sucrose polysoyate, sucrose ricinoleate, sucrose tetraisostearate, sucrose tribehenate, sucrose hexaoleate/hexapalmitate/hexastearate, sucrose hexapalmitate, sucrose trilaurate, and mixtures thereof.

In some embodiments, the sucrose fatty acid esters include sucrose oleate, sucrose laurate (and) aqua (and) alcohol, sucrose laurate, sucrose myristate, sucrose palmitate, sucrose polystearate, sucrose tristearate, sucrose distearate, sucrose stearate, and mixtures thereof, all of which are commercially available from Mitsubishi-Kagaku under the tradename Surfhope(R) C. The sucrose fatty acid ester may be used, for example, as a mixture with other ingredient, for example alcohol, such as the products sold, for example, by Mitsubishi-Kagaku under the trade name Surfhope(R) C. Alternatively the sucrose fatty acid ester may also be used without additives, for example, such as the product Ryoto Sugar Ester S 370 (Ryoto). Preferred sucrose fatty acid esters include sucrose oleate, sucrose stearate, sucrose distearate, sucrose tristearate, and mixtures thereof.

The sucrose fatty acid esters include sucrose fatty acid esters sold under the trade name D Ester®, produced by Dai-Ichi Kogyo Seiyaku Co., Ltd of Japan (which, in some examples, can be produced according to the methods described in U.S. Pat. Nos. 4,898,935, 4,996,309, 4,995,911, 5,011,922 and 5,017,697, and distributed through Montello Inc., Tulsa, Okla., such as the F-160 and F-140 grade esters sold under the trade name DK Ester®, and sucrose esters sold under the trade name SURFHOPE® SE PHARMA, by Mitsubishi-Kagaku Foods Corporation, distributed by Mitsubishi Chemical Performance Polymers, Inc. These sucrose fatty acid esters are mixtures of esters with different degrees of esterification. The sucrose fatty acid esters further include Ryoto sugar esters, which are food-grade esters sold by Mitsubishi-Kagaku Foods Corporation, distributed by Mitsubishi Chemical Performance Polymers, Inc. Exemplary sucrose fatty acid esters sold under the trade name DK Ester®, and those sold under the trade name SURFHOPE® SE PHARMA and Ryoto sugar esters, are listed in Table IB, below. The table lists the average degree of esterification or the fatty acid composition within the mixture, and the HLB of the sucrose fatty acid ester surfactant. Any of the surfactants in Table I B can be used. Typically, the surfactant (e.g., a surfactant listed in table I B), has an HLB value between at or about 14 and at or about 20, typically between at or about 15 and at or about 18, e.g., but not limited to, those surfactants in the table having an HLB of 15 or 16, such as the sucrose fatty acid ester surfactant sold under the name DK ESTER® F-160, produced by Dai-Ichi Kogyo Seiyaku Co., Ltd of Japan, and distributed through Montello Inc., Tulsa, Okla. Other exemplary sucrose fatty acid ester surfactants are described in Youan et al, AAPS PharmaSci 2003; 5(2) Article 22; 1-9 and in Okamoto et al, Biol. Pharm. Bull. 28(9): 1689-1694 (2005).

The sorbitan esters may be selected from the group consisting of sorbitan monostearate, sorbitan tristearate, sorbitan monolaurate, sorbitan monooleate, sorbitan palmitate or mixtures thereof.

The fatty alcohol esters include esters of $C_{6-22}$ fatty acids with a monohydric alcohol and/or esters of $C_{6-22}$ fatty alcohols with a monocarboxylic acid. Likewise, fatty alcohol esters may be esters of $C_{6-18}$ fatty acids with a monohydric alcohol and/or esters of $C_{6-18}$ fatty alcohols with a monocarboxylic acid. Non-limiting examples include butyl isostearate, butyl oleate, butyl octyl oleate, cetyl palmitate, cetyl octanoate, cetyl laurate, cetyl lactate, cetyl isononanoate, cetyl stearate, diisostearyl fumarate, diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisopropyl dimerate, triisostearyl trilinoleate, octodecyl stearoyl stearate, hexyl laurate, hexadecyl isostearate, hexydecyl laurate, hexyldecyl octanoate, hexyldecyl oleate, hexyldecyl palmitate, hexyldecyl stearate, isononyl isononanaote, isostearyl isononate, isohexyl neopentanoate, isohexadecyl stearate, isopropyl isostearate, n-propyl myristate, isopropyl myristate, n-propyl palmitate, isopropyl palmitate, hexacosanyl palmitate, lauryl lactate, octacosanyl palmitate, propylene glycol monolaurate, triacontanyl palmitate, dotriacontanyl palmitate, tetratriacontanyl palmitate, hexacosanyl stearate, octacosanyl stearate, triacontanyl stearate, dotriacontanyl stearate, stearyl lactate, stearyl octanoate, stearyl heptanoate, stearyl stearate, tetratriacontanyl stearate, triarachidin, tributyl citrate, triisostearyl citrate, tri-$C_{12-13}$-alkyl citrate, tricaprylin, tricaprylyl citrate, tridecyl behenate, trioctyldodecyl citrate, tridecyl cocoate, tridecyl isononanoate, glyceryl monoricinoleate, 2-octyldecyl palmitate, 2-octyldodecyl myristate or lactate, di(2-ethylhexyl)succinate, tocopheryl acetate, and mixtures thereof.

Non-ethoxylated, Sulfate-free Anionic Surfactants

The term "anionic surfactant" means a surfactant comprising, as ionic or ionizable groups, only anionic groups. In the present case, a species is termed as being "anionic" when it bears at least one permanent negative charge or when it can be ionized as a negatively charged species, under the conditions of use of the composition of the invention (for example the medium or the pH) and not comprising any cationic charge.

It is understood in the present description that:
carboxylate anionic surfactants comprise at least one carboxylic or carboxylate function (—COOH or —COO—) and may optionally also comprise one or more sulfate and/or sulfonate functions;
sulfonate anionic surfactants comprise at least one sulfonate function (—SO$_3$H or —SO$_3$—) and may optionally also comprise one or more sulfate functions, but do not comprise any carboxylate functions; and The carboxylic anionic surfactants that may be used thus comprise at least one carboxylic or carboxylate function (—COOH or —COO—). They may be chosen from the following compounds: acylglycinates, acyllactylates, acylsarcosinates, acylglutamates; alkyl-D-galactosideuronic acids, alkyl ether carboxylic acids, alkyl($C_{6-30}$ aryl) ether carboxylic acids, alkylamido ether carboxylic acids; and also the salts of these compounds; the alkyl and/or acyl groups of these compounds comprising from 6 to 30 carbon atoms, especially from 12 to 28, better still from 14 to 24 or even from 16 to 22 carbon atoms; the aryl group preferably denoting a phenyl or benzyl group; these compounds possibly being polyoxyalkylenated, especially polyoxyethylenated, and then preferably comprising from 1 to 50 ethylene oxide units and better still from 2 to 10 ethylene oxide units.

Use may also be made of the $C_6$-$C_{24}$ alkyl monoesters of polyglycoside-polycarboxylic acids, such as $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates, and salts thereof.

Among the above carboxylic surfactants, mention may be made most particularly of polyoxyalkylenated alkyl(amido) ether carboxylic acids and salts thereof, in particular those comprising from 2 to 50 alkylene oxide and in particular ethylene oxide groups, such as the compounds sold by the company KAO under the name AKYPO.

The polyoxyalkylenated alkyl (amido) ether carboxylic acids that may be used are preferably chosen from those of formula (1):

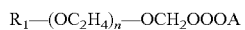

$R_1$—$(OC_2H_4)_n$—$OCH_2OOOA$ in which:
$R_1$ represents a linear or branched $C_6$-$C_{24}$ alkyl or alkenyl radical, an alkyl(C8-C9)phenyl radical, a radical $R_2CONH$—$CH_2$—$CH_2$— with $R_2$ denoting a linear or branched $C_9$-$C_{21}$ alkyl or alkenyl radical,
preferably, $R_1$ is a $C_8$-$C_{20}$ and preferably $C_8$-$C_{18}$ alkyl radical, and aryl preferably denotes phenyl,
n is an integer or decimal number (average value) ranging from 2 to 24 and preferably from 2 to 10,
A denotes H, ammonium, Na, K, Li, Mg or a monoethanolamine or triethanolamine residue.

It is also possible to use mixtures of compounds of formula (1), in particular mixtures of compounds containing different groups R1.

The polyoxyalkylenatedalkyl(amido) ether carboxylic acids that may be used are those of formula (1) in which:
R1 denotes a $C_{12}$-$C_{14}$ alkyl, cocoyl, oleyl, nonylphenyl or octylphenyl radical,
A denotes a hydrogen or sodium atom, and
n varies from 2 to 20 and preferably from 2 to 10.

Also, use may be made of compounds of formula (1) in which R denotes a $C_{12}$ alkyl radical, A denotes a hydrogen or sodium atom and n ranges from 2 to 10.

In some cases, the carboxylic anionic surfactants are chosen, alone or as a mixture, from:
acylglutamates, especially of $C_6$-$C_{24}$ or even $C_{12}$-$C_{20}$, such as stearoylglutamates, and in particular disodium stearoylglutamate;
acylsarcosinates, especially of $C_6$-$C_{24}$ or even $C_{12}$-$C_{20}$, such as palmitoylsarcosinates, and in particular sodium palmitoylsarcosinate;
acyllactylates, especially of $C_{12}$-$C_{28}$ or even $C_{14}$-$C_{24}$, such as behenoyllactylates, and in particular sodium behenoyllactylate;
$C_6$-$C_{24}$ and especially $C_{12}$-$C_{20}$ acylglycinates;
($C_6$-$C_{24}$)alkyl ether carboxylates and especially ($C_{12}$-$C_{20}$) alkyl ether carboxylates;
polyoxyalkylenated ($C_6$-$C_{24}$)alkyl(amido) ether carboxylic acids, in particular those comprising from 2 to 50 ethylene oxide groups;
in particular in the form of alkali metal or alkaline-earth metal, ammonium or amino alcohol salts.

The sulfonate anionic surfactants that may be used comprise at least one sulfonate function (—$SO_3H$ or —$SO_3$—).
They may be chosen from the following compounds:
alkylsulfonates, alkyla-midesulfonates, alkylarylsulfonates, α-olefinsulfonates, paraffin sulfonates, alkyl-sulfosuccinates, alkyl ether sulfosuccinates, alkylamidesulfosuccinates, alkyl-sulfoacetates, N-acyltaurates, acylisethionates; alkylsulfolaurates; and also the salts of these compounds;

the alkyl groups of these compounds comprising from 6 to 30 carbon atoms, especially from 12 to 28, better still from 14 to 24 or even from 16 to 22 carbon atoms;

the aryl group preferably denoting a phenyl or benzyl group.

In some cases, the sulfonate anionic surfactants are chosen, alone or as a mixture, from:
$C_6$-$C_{24}$ and especially $C_{12}$-$C_{20}$ alkylsulfosuccinates, especially laurylsulfosuccinates;
$C_6$-$C_{24}$ and especially $C_{12}$-$C_{20}$ alkyl ether sulfosuccinates;
($C_6$-$C_{24}$)acylisethionates and preferably ($C_{12}$-$C_{18}$) acylisethionates,
in particular in the form of alkali metal or alkaline-earth metal, ammonium or amino alcohol salts.

Useable isethionate surfactants include those according to the Formula below:

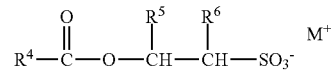

$$R^4-\overset{O}{\underset{\|}{C}}-O-\overset{R^5}{\underset{|}{CH}}-\overset{R^6}{\underset{|}{CH}}-SO_3^- \quad M^+$$

wherein,
$R^4$ is ($C_8$-$C_{22}$)alkyl;
$R^5$ and $R^6$ are each independently H or ($C_1$-$C_4$)alkyl; and
M+ is a sodium, potassium, or ammonium cation.

For example, isethionate surfactants include sodium lauroyl isethionate, sodium methyl lauroyl isethionate, sodium myristoyl isethionate, sodium cocoyl isethionate, sodium oleoyl isethionate, and ammonium oleoyl isethionate. Likewise, in some cases, the isethionate surfactant of (b) can be sodium cocoyl isethionate.

When the anionic surfactant is in salt form, the said salt may be chosen from alkali metal salts, such as the sodium or potassium salt, ammonium salts, amine salts and in particular amino alcohol salts, and alkaline-earth metal salts, such as the magnesium salt.

Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts may be used.

Thickening Agents

Consumers expect of their cleansing products have an aesthetically pleasing viscosity. Formulations that flow with a watery consistency are aesthetically unpopular to consumers with expectations of rich and creamy products. While low viscosity products may be effective for their intended purpose, they are perceived to be of low quality by the consumer. Formulations that flow with a watery consistency run off when applied.

As used herein, the term "thickening agent" means compounds which, by their presence, increase the viscosity of the composition into which they are introduced. For examples, the viscosity may be measured using a cone/plate viscometer, a Haake R600 rheometer, or the like. The thickening agent may be referred to interchangeably herein as thickener or rheology modifier. Thickening agents are also sometimes referred to as gellifying agents and/or viscosity modifying agents.

In certain embodiments, the thickening agent may be chosen from those conventionally used in cosmetics, such as polymers of natural origin and synthetic polymers, for example, nonionic, anionic, cationic, amphiphilic, or amphoteric polymers, and other known rheology modifiers, such as cellulose-based thickeners.

Many thickeners are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water.

In some cases, the thickening agents can be anionic thickening agents. Anionic thickening agents may be chosen from hydrophilic thickeners. Non-limiting examples of hydrophilic thickeners include homopolymers or copolymers of acrylic or methacrylic acids or the salts thereof and the esters thereof, such as those sold under the tradenames Versicol F® or Versicol K® by the company Allied Colloid, or under the tradename Ultrahold 8® by the company Ciba-Geigy; polyacrylates and polymethacrylates such as copolymers of (meth)acrylic acid, copolymers of (meth) acrylic acid, methylacrylate and dimethyl meta-isopropenyl benzyl isocyanate of ethoxylated alcohols such as methylacrylate and dimethyl meta-isopropenyl benzyl isocyanate of ethoxylated alcohol (INCI name: Polyacrylate-3) sold under the tradename Viscophobe® DB 1000 from The Dow Chemical Company, those sold under the tradenames Lubrajel and Norgel by the company Guardian, or under the tradename Hispajel by the company Hispano Chimica; and polyacrylic acids of Synthalen® K type, copolymers of acrylic acid and of acrylamide sold in the form of the sodium salt thereof, such as those sold under the tradenames Reten® by Hercules, sodium polymethacrylate such as those sold under the tradename Darvan® 7 by the company Vanderbilt, and the sodium salts of polyhydroxycarboxylic acids such as those sold under the tradename Hydagen F® by the company Henkel, and polyacrylic acid/alkyl acrylate copolymers of Pemulen™ type.

In certain cases, the at least one thickening agent is chosen from copolymers resulting from the polymerization of at least one monomer (a) chosen from carboxylic acids possessing α,β-ethylenically unsaturated groups or their esters, with at least one monomer (b) possessing ethylenically unsaturated groups and comprising a hydrophobic group.

The thickening agents may also be chosen from hydrophilic thickeners, for example cellulose polymers and gums, modified or unmodified carboxyvinyl polymers, such as those sold under the tradename Carbopol® (CTFA name: carbomer) by the company Goodrich, polyacrylamides, copolymers of acrylic acid and of acrylamide sold in the form of the sodium salt thereof, such as those sold under the tradenames Reten® by Hercules, and the sodium salts of polyhydroxycarboxylic acids such as those sold under the tradename Hydagen F® by the company Henkel, optionally crosslinked and/or neutralized 2-acrylamido-2-methylpropanesulphonic acid polymers and copolymers, for instance poly(2-acrylamido-2-methylpropanesulphonic acid) such as those sold under the tradename Hostacerin® AMPS (CTFA name: ammonium polyacryldimethyltauramide) by the company Clariant, crosslinked anionic copolymers of acrylamide and of AMPS, e.g. in the form of a water-in-oil emulsion, such as those sold under the tradename Simugel™ 600 (CTFA name: Acrylamide/Sodium acryloyldimethyltaurate copolymer/Isohexadecane/Polysorbate 80) by the company Seppic, polyacrylic acid/alkyl acrylate copolymers of Pemulen™ type, and mixtures thereof.

In some cases, the thickening agent may be chosen from nonionic homopolymers or copolymers containing ethylenically unsaturated monomers of the amide type, for example, the polyacrylamide products sold under the tradenames Cyanamer® P250 by the company CYTEC.

The thickening agents may be chosen from polymers of natural origin and may include thickening polymers comprising at least one sugar unit, for instance nonionic guar gums, optionally modified with C1-C6 hydroxyalkyl groups; biopolysaccharide gums of microbial origin, such as scleroglucan gum (also known as sclerotium gum) or xanthan gum; gums derived from plant exudates, such as gum arabic, ghatti gum, karaya gum, gum tragacanth, carrageenan gum, agar gum, carob gum, *ceratonia siliqua* gum or *cyamopsis tetragonoloba* (guar) gum; pectins; alginates; starches; hydroxy(C1-C6)alkylcelluloses; or carboxy(C1-C6)alkylcelluloses.

In some instances, the nonionic, unmodified guar gums may be chosen from GUARGEL D/15 sold by the company NOVEON, VIDOGUM GH 175 sold by the company UNIPECTINE, MEYPRO-GUAR 50 sold by the company MEYHALL, or Jaguar® C sold by the company RHODIA CHIMIE. In other instances, the nonionic modified guar gums may be chosen from Jaguar® HP8, HP60, HP120, DC 293 and HP 105 sold by the companies MEYHALL and RHODIA CHIMIE or Galactasol™ 4H4FD2 sold by the company Ashland.

Also, the thickening agents may be chosen from scleroglucans, for example, Actigum™ CS from Sanofi Bio Industries; Amigel® sold by the company Alban Muller International; xanthan gums, for instance Keltrol®, Keltrol® T, Keltrol® Tf, Keltrol® Bt, Keltrol® Rd, and Keltrol® Cg sold by the company CP Kelco, Rhodicare® S and Rhodicare® H sold by the company Rhodia Chimie; starch derivatives, for instance Primogel® sold by the company Avebe; hydroxyethylcelluloses such as Cellosize® QP3L, QP4400H, QP30000H, HEC30000A and Polymer PCG10 sold by the company Amerchol, Natrosol™ 250HHR, 250MR, 250M, 250HHXR, 250HHX, 250HR, and 250 HX, sold by the company Hercules, or Tylose® H1000 sold by the company Hoechst; hydroxypropylcelluloses, for instance Klucel™ EF, H, LHF, MF, and G, sold by the company Ashland; carboxymethylcelluloses, for instance Blanose® 7M8/SF, refined 7M, 7LF, 7MF, 9M31F, 12M31XP, 12M31P, 9M31XF, 7H, 7M31, and 7H3SXF, sold by the company Ashland, Aquasorb® A500 sold by the company Hercules, Ambergum® 1221 sold by the company Hercules, Cellogen® HP810A and HP6HS9 sold by the company Montello and Primellose® sold by the company Avebe.

In other cases, the modified nonionic guar gums may, for example, be modified with C1-C6 hydroxyalkyl groups. Such hydroxyalkyl groups may be chosen from hydroxymethyl, hydroxyethyl, hydroxypropyl, and hydroxybutyl groups.

Guar gums may be prepared by reacting the corresponding alkylene oxides, such as for example propylene oxides, with guar gum so as to obtain a guar gum modified with hydroxypropyl groups. The hydroxyalkylation ratio, which corresponds to the number of alkylene oxide molecules consumed to the number of free hydroxyl functional groups present on the guar gum, may in certain embodiments range from about 0.4 to about 1.2.

Examples of nonionic guar gums, optionally modified with hydroxyalkyl groups, include those sold under the tradenames Jaguar® HP8, Jaguar® HP60, Jaguar® HP120, Jaguar® DC 293, and Jaguar® HP 105 by the company Rhodia Chimie, and under the tradename Galactasol™ 4H4FD2 by the company Ashland.

In other cases, the guar gum may be chosen from those modified with a quaternary ammonium group, such as guar hydroxypropyltrimonium chloride, also sold under the tradename Jaguar® C-13S by the company Rhodia Chimie.

In other cases, the celluloses may be chosen from hydroxyethylcelluloses and hydroxypropylcelluloses, such as those sold under the tradenames Klucel™ EF, Klucel™ H, Klucel™ LHF, Klucel™ MF, Klucel™ G, by the company Ashland and under the tradename Cellosize™ PCG-10 by the company Amerchol.

In other cases, non-limiting thickening polysaccharides may be chosen from glucans; modified or unmodified starches such as those derived, for example, from cereals such as wheat, corn or rice, vegetables such as golden pea, or tubers such as potato or cassava; amylose, amylopectin, glycogen, dextrans, celluloses or derivatives thereof (methylcelluloses, hydroxyalkylcelluloses, ethylhydroxyethylcelluloses), mannans, xylans, lignins, arabans, galactans, galacturonans, chitin, chitosans, glucoronoxylans, arabinoxylans, xyloglucans, glucomannans, pectic acids or pectins, arabinogalactans, carrageenans, agars, gums arabic, gums tragacanth, Ghatti gums, Karaya gums, carob gums, galactomannans such as guar gums and their nonionic derivatives such as hydroxypropylguar, or mixtures thereof.

In other cases, the thickening agent may be chosen from silicas or hydrophobic silicas, such as those described in EP-A-898960, incorporated by reference herein. Examples of such silicas include those sold under the tradename Aerosil® R812 by the company Degussa, CAB-O-SIL® TS-530, CAB-O-SIL® TS-610, CAB-O-SIL® TS-720 by the company Cabot, or Aerosil® R972 and Aerosil® R974 by the company Degussa; clays, such as montmorillonite; modified clays such as the bentones, for example, stearalkonium hectorite, stearalkonium bentonite; or polysaccharide alkyl ethers, optionally with the alkyl group having from 1 to 24 carbon atoms, for example from 1 to 10 carbon atoms, from 1 to 6 carbon atoms, or from 1 to 3 carbon atoms, such as those described in document EP-A-898958, incorporated by reference herein.

In certain cases, when an anionic thickening agent is used, it is generally neutralized before being included in, or as it is added to the compositions of the disclosure. Such an anionic thickening agent may be neutralized by employing traditional neutralizing agents such as alkanolamines, for example, monoethanolamine and diethanolamine; aminomethyl propanol; basic amino acids, for example arginine and lysine; or ammonium compounds and their salts. The anionic thickening agent may also be neutralized by a latex polyurethane polymer having at least one free amino group.

In particular, the at least one thickening agent is selected from cellulose polymers, gums, modified or unmodified carboxyvinyl polymers, polyacrylamides, copolymers of acrylic acid and of acrylamide, sodium salts of polyhydroxycarboxylic acids, optionally crosslinked and/or neutralized 2-acrylamido-2-methylpropanesulphonic acid polymers and copolymers, polyacrylic acid/alkyl acrylate, glucans, modified or unmodified starches, silicas, and mixtures thereof.

The thickening agent may be a starch derivative chosen from the compounds of the following formulae:

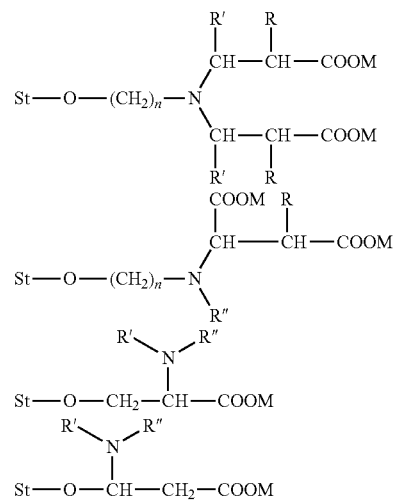

in which formulae:
St-O represents a starch molecule,
R, which may be identical or different, represents a hydrogen atom or a methyl radical,
R', which may be identical or different, represents a hydrogen atom, a methyl radical or a —COOH group,
n is an integer equal to 2 or 3,
M, which may be identical or different, denotes a hydrogen atom, an alkali metal or alkaline-earth metal such as Na, K or Li, $NH_4$, a quaternary ammonium or an organic amine,
R" represents a hydrogen atom or an alkyl radical containing from 1 to 18 carbon atoms.

These compounds are disclosed in particular in U.S. Pat. Nos. 5,455,340 and 4,017,460 which are incorporated by way of reference in their entirety.

The starch molecules may be derived from any plant sources of starch such as, in particular, corn, potato, oat, rice, tapioca, sorghum, barley or wheat. The starch hydrolysates mentioned above may also be used.

Amphoteric Surfactants

Amphoteric surfactants useful in the cosmetic compositions disclosed herein may be chosen from betaines, sultaines, amphoacetates, amphoprionates, and mixtures thereof. More typically, betaines and amphoprionates are used, and most typically betaines. Betaines which can be used in the current compositions include those having the formulas below:

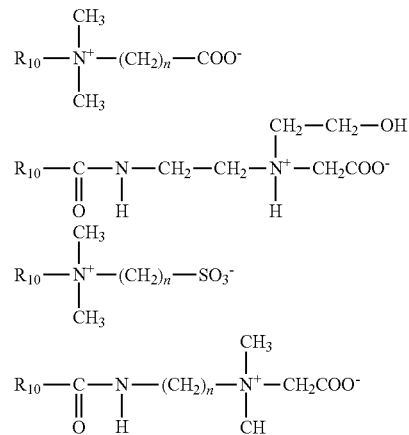

wherein

R$^{10}$ is an alkyl group having 8-18 carbon atoms; and n is an integer from 1 to 3.

Particularly useful betaines include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocoamidopropyl betaine, behenyl betaine, capryl/capramidopropyl betaine, lauryl betaine, and mixtures thereof, and more typically coco betaine.

Hydroxyl sultaines useful in the compositions of the invention include the following

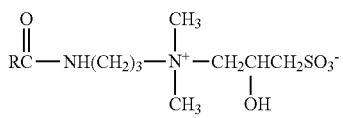

wherein

R is an alkyl group having 8-18 carbon atoms.

Useful alkylamphoacetates include those having the formula

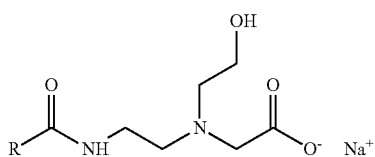

wherein

R is an alkyl group having 8-18 carbon atoms.

useful alkyl amphodiacetates include those having the formula

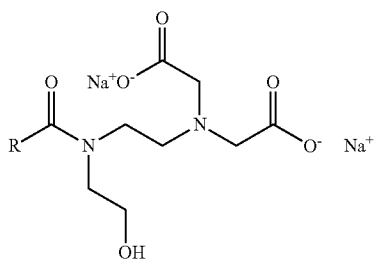

wherein

R is an alkyl group having 8-18 carbon atoms.

The amphoteric surfactants of the present disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of (C$_8$-C$_{20}$)alkylbetaines, (C$_8$-C$_{20}$)alkylamido (C$_1$-C$_6$)alkylbetaines, sulfobetaines, (C$_8$-C$_{20}$)alkylsulfobetaines, (C$_8$-C$_{20}$)alkylamido (C$_1$-C$_6$)alkylsulfobetaines, (C$_8$-C$_{20}$)alkylamphoacetate, (C$_8$-C$_{20}$)alkylamphodiacetate, and mixtures thereof.

Among the optionally quaternized secondary or tertiary aliphatic amine derivatives that may be used, mention may also be made of the products of respective structures (A1) and (A2) below:

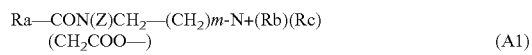

in which:

Ra represents a C$_{10}$-C$_{30}$ alkyl or alkenyl group derived from an acid Ra—COOH preferably present in hydrolysed coconut oil, a heptyl group, a nonyl group or an undecyl group, Rb represents a β-hydroxyethyl group, Rc represents a carboxymethyl group;

m is equal to 0, 1 or 2,

Z represents a hydrogen atom or a hydroxyethyl or carboxymethyl group;

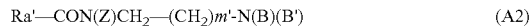

in which:

B represents —CH$_2$CH$_2$OX', with X' representing —CH$_2$—COOH, CH$_2$—COOZ', CH$_2$CH$_2$—COOH, —CH$_2$CH$_2$—COOZ', or a hydrogen atom, B' represents —(CH$_2$)z-Y', with z=1 or 2, and Y' representing COOH, COOZ', CH$_2$—CHOH—SO$_3$H or —CH$_2$—CHOH—SO$_3$Z', m' is equal to 0, 1 or 2, Z represents a hydrogen atom or a hydroxyethyl or carboxymethyl group, Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropa-nolamine or triisopropanolamine, 2-amino-2-methyl-1-propanol, 2-amino-2-methyl-1,3-propanediol and tris(hydroxymethyl) aminomethane, Ra' represents a C$_{10}$-C$_{30}$ alkyl or alkenyl group of an acid Ra'COOH preferably present in hydrolysed linseed oil or coconut oil, an alkyl group, in particular a C$_{17}$ alkyl group, and its iso form, or an unsaturated C$_{17}$ group.

Among the compounds corresponding to formula (A2) in which X' represents an hydrogen atom, mention may be made of compounds classified in the CTFA dictionary, under the names sodium cocoamphoacetate, sodium lauroamphoacetate, sodium caproamphoacetate and sodium capryloamphoacetate.

Other compounds corresponding to formula (A2) are disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodi-propionate, lauroamphodipropionic acid and cocoamphodipropionic acid.

Examples that may be mentioned include the cocoamphodiacetate sold by the company Rhodia under the trade name Miranol® C2M Concentrate, the sodium cocoamphoacetate sold under the trade name Miranol Ultra C 32 and the product sold by the company Chimex under the trade name CHIMEXANE HA.

Use may also be made of the compounds of formula (A3):

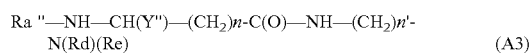

in which:

Ra" represents a C10-C30 alkyl or alkenyl group of an acid Ra"—C(O)OH preferably present in hydrolysed linseed oil or coconut oil;

Y" represents the group —C(O)OH, —C(O)OZ", —CH$_2$—CH(OH)—SO$_3$H or the group CH$_2$—CH(OH)—SO$_3$—Z", with Z" representing a cationic counterion resulting from an alkali metal or alkaline-earth metal, such as sodium, an ammonium ion or an ion resulting from an organic amine;

Rd and Re represent, independently of each other, a $C_1$-$C_4$ alkyl or hydroxyalkyl radical; and n and n' denote, independently of each other, an integer ranging from 1 to 3.

Among the compounds corresponding to formula (A3), mention may in particular be made of the compound classified in the CTFA dictionary under the name sodium diethylaminopropylcocoaspartamide, such as the one sold by the company Chimex under the name CHIMEXANE HB.

Preferably, the amphoteric surfactants are chosen from ($C_8$-$C_{20}$)alkylbetaines, ($C_8$-$C_{20}$)alkylamido($C_1$-$C_6$)alkylbetaines, ($C_8$-$C_{20}$)alkylamphoacetates and ($C_8$-$C_{20}$)alkylamphodiacetates, and mixtures thereof.

In some cases, the at least one amphoteric surfactant is chosen from ($C_8$-$C_{20}$)alkyl betaines, ($C_8$-$C_{20}$)alkylamido($C_1$-$C_6$)alkylbetaines, ($C_8$-$C_{20}$)alkylamphoacetate, ($C_8$-$C_{20}$) alkylamphodiacetate, and their salts, and mixtures thereof. In some cases, the at least one amphoteric surfactant is selected from coco-betaine, cocamidopropylbetaine, sodium cocoamphoacetate, disodium cocoamphodiacetate, and mixtures thereof.

Conditioning Polymers

The conditioning polymer may be a nonionic polymer, for example, polyalkyloxazolines, vinyl acetate homopolymers, acrylic ester and vinyl acetate copolymers, ethylene and vinyl acetate copolymers, copolymers of vinyl acetate and maleic ester, maleic anhydride and polyethylene copolymers, homopolymers of alkyl acrylates and the homopolymers of alkyl methacrylates, copolymers of acrylic esters, copolymers of acrylonitrile and of a nonionic monomeric unit chosen from butadiene and alkyl (meth)acrylates; and copolymers of alkyl acrylate and urethane.

The conditioning polymer may be a cationic polymer. Cationic conditioning polymers can be chosen from those comprising units of at least one amine group chosen from primary, secondary, tertiary and quaternary amine groups that may either form part of the main polymer chain, or be borne by a side substituent that is directly attached to the main polymer chain. Such cationic polymers generally have a number average molecular mass ranging from 500 to $5 \times 10^6$, or more preferably from 1000 to $3 \times 10^6$. Polymers of the polyamine, polyamino amide and polyquaternary ammonium type that may be used include but are not limited to:

1) homopolymers and copolymers derived from acrylic or methacrylic esters or amides. Copolymers of these polymers can also comprise at least one unit derived from comonomers which may be chosen from the family of acrylamides, methacrylamides, diacetone acylamides, acrylamides and methacrylicamides substituted on the nitrogen with at least one group chosen from lower (C1 C4) alkyls, acrylic and methacrylic acids and esters thereof, vinylactams such as vinylpyrrolidone and vinylcaprolactam, and vinyl esters. Examples of such polymers include:

Copolymers of acrylamide and of methacryloyloxyethyltrimethylammonium methosulfate, examples of which include polymers known via the INCI nomenclature as Polquaternium-5, such as the products sold under the names RETEN 210, RETEN 220, RETEN 230, RETEN 240, RETEN 1104, RETEN 1105, RETEN 1006 by the company Hercules and MERQUAT 5, MERQUAT 5 SF by the company Nalco.

Copolymers of vinylpyrrolidone and dimethylaminopropyl methacrylamide, examples of which include polymers known via the INCI nomenclature as Polyquaternium-28, such as the products sold under the name GAFQUAT HS-100 by the company International Speciality Products (ISP).

Copolymers of vinyl pyrrolidone and dialkyaminoalkyl acrylates or methactylates, examples of which include polymers known via the INCI nomenclature as Polquaternium-11, such as the products sold under the name Gafquat 440, Gafquat 734, Gafquat 755, Gafquat 755N by the company International Speciality Products (ISP), and Luviquat PQ11 PM by the company BASF and Polyquat-11 SL by the company Sino Lion.

Copolymers vinylpyrrolidone, dimethylaminopropyl methacrylamide and methacryloylaminopropyl lauryldimonium chloride, examples of which include polymers known via the INCI nomenclature as polyquaternium-55, such as the products sold under the name Styleze W-20 by the company International Speciality Products (ISP).

Copolymers of acrylic acid, acrylamide and methacrylamidopropyltrimonium chloride, examples of which include polymers known via the INCI nomenclature as Polyquaternium-53, such as the products sold under the name MERQUAT 2003 by the company Nalco.

Copolymers of dimethyaminopropylacrylate (DMAPA), acrylic acid and acrylonitrogens and diethyl sulfate, examples of which include polymers known via the INCI nomenclature as Polyquaternium-31, such as the products sold under the name HYPAN QT100 by the company Lipo.

Copolymers of acrylamide, acrylamidopropyltrimonium chloride, 2-amidopropylacrylamide sulfonate, and dimethyaminopropylacrylate (DMAPA), examples of which include polymers known via the INCI nomenclature as polyquaternium43, such as the products sold under the name BOZEQUAT 4000 by the company Clairant.

Copolymers of acrylic acid, methylacrylate and methacrylamidopropyltrimonium chloride, examples of which include polymers known via the INCI nomenclature as Polyquaternium-47, such as the products sold under the name MERQUAT 2001 and MERQUAT 2001N sold commercially by Nalco.

Copolymers of methacryloyl ethyl betaine, 2-hydroxyethyl methacrylate and methacryloyl ethyl trimethyl ammonium chloride, examples of which include polymers known via the INCI nomenclature as Polyquaternium-48, such as the products sold under the name PLASCIZE L450 by the company Goo Chemical.

Copolymers of acrylic acid diallyl dimethyl ammonium chloride and acrylamide, examples of which include polymers known via the INCI nomenclature as polyquaternium 39, such as the products sold under the name MERQUAT 3330 and MERQUAT 3331 by the company Nalco.

Further examples include copolymers of methacrylamide methacrylamidopropyltrimonium and methacryloylethyltrimethyl ammonium chloride and their derivatives, either homo or copolymerised with other monomers, examples of which include polymers known via the INCI nomenclature as: Polyquaternium-8, Polyquaternium-9, Polyquaternium-12, Polyquaternium-13 Polyquaternium-14, Polyquaternium-15, such as the products sold under the name ROHAGIT KF 720 F by the company Rohm, Polyquaternium-30, such as the products sold under the name MEXOMERE PX by the company Chimex, Polyquatemium-33, Polyquaternium-35, Polyquaternium-36, such as the products sold under the name PLEX 3074 L by the company Rhon, Polyquaternium 45, such as the products sold under the name PLEX 3073L by the company Rohn, Polyquaternium 49, such as the products sold under the name PLASCIZE L440 by the company Goo Chemicals, Polyquaternium 50 such as the products sold under the name PLASCIZE L441 by the company Goo Chemicals, Polyquaternium-52.

2) Cationic polysaccharides, such as cationic celluloses and cationic galactomannan gums. Among the cationic polysaccharides that may be mentioned, for example, are cellulose ether derivatives comprising quaternary ammonium groups and cationic cellulose copolymers or cellulose derivatives grafted with a water-soluble quaternary ammonium monomer and cationic galactomannan gums. Examples include but are not limited to:

Copolymers of hydroxyethylcelluloses and diallyldimethyl ammonium chlorides, examples of which include polymers known via the INCI nomenclature as Polyquaternium-4, such as the products sold under the name CELQUAT L 200 and CELQUAT H 100 by the company National Starch.

Copolymers of hydroxyethylcelluloses and a trimethyl ammonium substituted epoxide, examples of which include polymers known via the INCI nomenclature as Polyquaternium-10, such as the products sold under the name AEC Polyquaternium-10 by the company A&E Connock, CATINAL C-100 CATINAL HC-35 CATINAL HC-100 CATINAL HC-200 CATINAL LC-100 CATINAL LC-200 by the company Toho, CELQUAT SC-240C CELQUAT SC-230M, by the company National Starch, DEKAQUAT 400, DEKAQUAT 3000 by the company Dekker, LEOGARD G P by the company Akzo Nobel, RITA POLYQUTA 400 RITA, POLYQUTA 3000 by the company RITA, UCARE Polymer JR-125 UCARE Polymer JR-400 UCARE Polymer JR-30M UCARE Polymer LK UCARE Polymer LR 400 UCARE Polymer LR 30M by the company Amerchol.

Copolymers of hydroxyethylcelluloses and lauryl dimethyl ammonium substituted epoxides, examples of which include polymers known via the INCI nomenclature as Polyquaternium-24, such as the products sold under the name QUATRISOFT polymer LM-200 by the company Amerchol.

Derivatives of Hydroxypropyl Guar, examples of which include polymers known via the INCI nomenclature as Guar Hydroxypropyltrimonium Chloride, such as the products sold under the name CATINAL CG-100, CATINAL CG-200 by the company Toho, COSMEDIA GUAR C-261N, COSMEDIA GUAR C-261N, COSMEDIA GUAR C-261N by the company Cognis, DiaGum P 5070 by the company Freedom Chemical Diamalt, N-HANCE CATIONIC GUAR by the company Hercules/Aqualon, HI-CARE 1000, JAGUAR C-17, JAGUAR C-2000, JAGUAR C-13S, JAGUAR C-14S, JAGUAR EXCEL by the company Rhodia, Kiprogum CW, Kiprogum NGK by the company Nippon Starch.

Hydroxypropyl derivatives of Guar Hydroxypropyltrimonium Chloride, examples of which include polymers known via the INCI nomenclature as Hydroxypropyl Guar Hydroxypropyltrimonium Chloride, such as the products sold under the name JAGAUR C-162 by the company Rhodia.

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Non-limiting examples of such derivatives include the adipic acid/epoxypropyl/diethylenetriamine.

5) Cyclopolymers of dialkdiallylamine or of dialkyldiallyammonium, among which polymers mention may be made of:

Dimethyldiallyammonium chloride polymers, examples of which include polymers known via the INCI nomenclature as Polyquaternium-6, such as the products sold under the name MERQUAT 100 by the company Nalco, MIRAPOL 100 by the company Rhodia, RHEOCARE CC6 by the company Cosmetic Rheologies, AEC polyquaternium-6 by the company A&E Connock, AGEQUAT 400 by the company CPS, CONDITIONER P6 by the company 3V Inc., FLOCARE C106 by the company SNF, GENAMIN PDAC by the company Clariant, MACKERNIUM 006 by the company McIntyre.

Copolymers of acrylamides and dimethyldiallyammonium chlorides monomers, examples of which include polymers known via the INCI nomenclature as Polyquaternium-7, such as the products sold under the name AEC Polyquaternium-7 by the company A&E Connock, AGEQUAT-5008, AGEQUAT C-505 by the company CPS, Conditioner P7 by the company 3V Inc. FLOCARE C 107 by the company SNF MACKERNIUM 007, MACKERNIUM 007S by the company McIntyre, ME Polymer 09W by the company Toho, MERQUAT 550, MERQUAT 2200, MERQUAT S by the company Nalco, MIRAPOL 550 by the company Rhodia, RHEOCARE CC7, RHEOCARE CCP7 by the company Cosmetic Rheologies, SALCARE HSP-7, SALCARE SC10, SALCARE SUPER 7 by the company Ciba.

Copolymers of dimethyldiallylammoniumchlorides and acrylic acids, examples of which include polymers known via the INCI nomenclature as polyquaternary-22, such as the products sold under the name MERQUAT 280 and MERQUAT 295 by the company Nalco.

6) Quaternary diammonium polymers comprising repeat units corresponding to [—N+($R^1$)($R^2$)-$A^1$-N+($R^3$)($R^4$)-$B^1$-][2X—], in which $R^1$, $R^2$, $R^3$ and $R^4$, which may be identical or different, are chosen from aliphatic, alicyclic and arylaliphatic radicals comprising from 1 to 20 carbon atoms and from lower hydroxyalkylaliphatic radicals, or $R^1$, $R^2$, $R^3$ and $R^4$, together or separately, constitute, with the nitrogen atoms to which they are attached, heterocycles optionally comprising a second heteroatom other than nitrogen, or $R^1$, $R^2$, $R^3$ and $R^4$, are chosen from liner or branched $C_1$-$C_6$ alkyl radicals substituted with at least one group chosen from nitrile, ester, acyl and amide groups and groups of —CO—O—$R^5$-D and —CO—NH—$R^5$-D wherein $R^5$ is chosen from alkylene groups and D is chosen from quaternary ammonium groups. $A^1$ and $B^1$, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X— is an anion derived from inorganic and organic acids. D is chosen from a glycol residue, a bis-secondary diamine residue, a bis-primary diamine residue or a ureylene group. An example of which include polymers known via the INCI nomenclature as Hexadimethrine chloride, where $R^1$, $R^2$, $R^3$ and $R^4$ are each methyl radicals, $A^1$ is $(CH_2)_3$ and B1 is $(CH_2)6$ and X=C1. Further examples of which include polymers known via the INCI nomenclature as polyquaternium-34 where $R^1$ and $R^2$ are ethyl radicals and $R^3$ and $R^4$ are methyl radicals and $A^1$ is $(CH_2)_3$ and $B^1$ is $(CH_2)_3$ and X=Br, such as the products sold under the name MEXOMERE PAX by the company ChimEx.

7) Polyquaternary ammonium polymers comprising repeating units of formula [—N+($R^6$)($R^7$)—$(CH_2)$r-NH—CO—$(CH_2)_q$—(CO)t-NH—$(CH2)_s$-N+($R^8$)($R^9$)-A-] [2X—], in which $R^6$, $R^7$, $R^8$ and $R^9$ which may be identical or different, are chosen from a hydrogen atom and a methyl, ethyl, propyl, hydroxyethyl, hydroxypropyl, and —$CH_2CH_2$$(OCH_2CH_2)_p$OH radicals, wherein p is equal to 0 or an integer ranging from 1 to 6, wherein $R^6$, $R^7$, $R^8$ and $R^9$ do not all simultaneously represent a hydrogen atom. R and s which may be identical or different are each an integer ranging from 1 to 6, q is equal to 0 or an integer ranging from 1 to 34 and X— is anion such as a halide. T is an integer chosen to be equal to 0 or 1. A is chosen from divalent radicals such as —$CH_2$—$CH_2$—O—$CH_2$—$CH_2$—. Examples of which include:

Polymers known via the INCI nomenclature as polyquaternium-2, where r=s=3, q=0, t=0, $R^6$, $R^7$, $R^8$ and $R^9$ are methyl groups, and A is —$CH_2$—$CH_2$—O—$CH_2$—$CH_2$, such as the products sold under the name ETHPOL PQ-2 from ETHOX and MIRAPOL A-15 by the company Rhodia.

Polymers known via the INCI nomenclature as polyquaternium-17 where r=s=3, q=4, t=1 $R^6$, $R^7$, $R^8$ and $R^9$ are methyl groups, and A is —$CH_2$—$CH_2$—O—$CH_2$—$CH_2$.

Polymers known via the INCI nomenclature as Polyquaternium 18, where r=s=3, q=7, t=1 $R^6$, $R^7$, $R^8$ and $R^9$ are methyl groups, and A is —$CH_2$—$CH_2$—O—$CH_2$—$CH_2$.

Polymers known via the INCI nomenclature as the block copolymer formed by the reaction of Polyquaternium-2 with Polyquaternium-17, known as Polyquaternium 27, such as the products sold under the name MIRAPOL 175 by the company Rhodia.

8) Copolymers of vinylpyrrolidones and of vinylimidazoles and optionally vinylcaprolactums, examples of which include polymers known via the INCI nomenclature as Polyquaternary-16 formed from methylvinylimidazolium chlorides and vinylpyrrolidones, such as the products sold under the name LUVIQUAT FC370, LUVIQUAT FC550, LUVIQUAT FC905, LUVIQUAT HM-552 by the company BASF. Or copolymers of vinylcaprolactams and vinylpyrrolidones with methylvinylimidazolium methosulfates, examples of which include polymers known via the INCI nomenclature as Polyquaternium-46, such as the products sold under the name LUVIQUAT Hold by the company BASF. Or copolymers of vinylpyrrolidones and quaternized imidazolines, examples of which include polymers known via the INCI nomenclature polyquaternary 44, such as the products sold under the name LUVIQUAT CARE by the company BASF 9) Polyamines such as the product POLYQUART H sold by COGNIS under the reference name polyethylene glycol (15) tallow polyamine in the CTFA dictionary.

10) Cross linked methacryloyloxy(C1-C4)alkyltri(C1-C4)alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, examples of which include polymers known via the INCI nomenclature as Polyquaternium-37, such as the products sold under the name SYNTHALEN, CN SYNTHALEN CR, SYNTHALEN CU, sold by 3V SIGMA, or as a dispersion in another media such as the products sold under the name SALCARE SC95 and SALCARE SC96 by the company Ciba or RHEOCARE CTH(E) by the company Cosmetic Rheologies. Or in another example of which include polymers known via the INCI nomenclature as Polyquaternium-32, or when sold as a dispersion in mineral oil such as the products sold under the name SALCARE SC92 by the company Ciba.

11) Further examples of cationic polymers include polymers known via the INCI nomenclature as Polyquaternium 51, such as the products sold under the name LIPIDURE-PMB by the company NOF, via the INCI nomenclature as Polyquaternium 54, such as the products sold under the name QUALTY-HY by the company Mitsui, and via the INCI nomenclature as Polyquaternium 56 such as the products sold under the name HAIRROL UC4 by the company Sanyo chemicals.

12) Silicone polymers comprising cationic groups and/or groups which may be ionised into cationic groups. For example: cationic silicones of the general formula ($R^{10}$—N+$(CH_3)_2$)—$R^{11}$—$(Si(CH_3)_2$—O$)_x$—$R^{11}$—(N+$(CH_3)_2$)—$R^{10}$), where $R^{10}$ is an alkyl derived from coconut oil, and $R^{11}$ is $(CH_2CHOCH_2O(CH_2)_3$ and x is a number between 20 and 2000, examples of which include polymers known by the INCI nomenclature as QUATERNIUM 80, such as the products sold under the name as ABIL QUAT 3272 and ABIL QUAT 3474 sold commercially by Goldschmidt.

Silicones containing groups which may be ionised into cationic groups, for example aminosilicones containing at least 10 repeating siloxane —$(Si(CH_3)_2$—O) units within the polymer chain, with either terminal, graft or a mixture of terminal and graft aminofunctional groups. Example functional groups are not limited to aminoethylaminopropyl, aminoethylaminoisobutyl, aminopropyl. In the case of graft polymers, the terminal siloxane units can either be $(CH_3)_3$Si—O or R12$(CH_3)_2$Si—O, where R12 can be either OH or OR13, where R13 is a C1 C8 alkyl group, or a mixture of both functional terminal groups. These silicones are also available as preformed emulsions. Polymer with terminal siloxane units of $(CH3)3Si$—O examples of which include polymers known by the INCI nomenclature as trimethylsilylamodimethicone, such as the products sold under the name as DC-2-8566, DC 7224 and DC-2-8220 sold commercially by Dow Corning and SF1708 and SM 2125 sold commercially by GE Silicones and Wacker Belsil ADM 653 sold commercially by Wacker silicones. Further examples include polymers with terminal siloxane units of (R12O)$(CH_3)_2$Si—O where R12 can be either OH or OR13, where R13 is a C1 C8 alkyl group, or a mixture of both functional terminal groups, known by the INCI nomenclature as amodimethicone, such as the products sold under the name as WACKER BELSIL ADM 1100, WACKER BELSIL ADM 1600, y ADM 652, WACKER BELSIL ADM 6057E, WACKER BELSIL ADM 8020 sold commercial by Wacker Silicones, DC929, DC939 and DC949 sold commercially by Dow Corning and SM2059 sold commercially by GE silicones.

Silicones containing groups which may be ionised into cationic groups—for example silicones containing at least 10 repeating siloxane —$Si(CH_3)_2$—O) units within the polymer chain, with either terminal, graft or a mixture of terminal and graft am inofunctional groups, together with additional functional groups.

Implementation of the present disclosure is provided by way of the following examples. The examples serve to illustrate the technology without being limiting in nature.

EXAMPLE 1

Formulations (Formulations)

| | INCI US Name | A | B | C | D | E | F | G |
|---|---|---|---|---|---|---|---|---|
| (a) | Decyl Glucoside | 13.3 | 13.3 | 8 | 5.3 | 5.3 | 5.3 | 3.71 |
| (b) | Glyceryl Oleate, Sucrose Stearate, and/or Sucrose Cocoate | 1.3 | 2 | 2 | 2 | 2 | 3 | 2 |
| (c) | Sodium Lauroyl Sarcosinate and/or Sodium Lauroyl Methyl Isethionate | 3.4 | 3.4 | 10.4 | 6.2 | 6.2 | 6.2 | 6.8 |
| (d) | Gellan Gum and/or Sclerotium Gum | 0.6 | 0.6 | 0.6 | 0.2 | 0.2 | 0.2 | — |
| (d) | Hydroxypropyl Guar Hydroxypropyl trimonium Chloride | 0.7 | 0.7 | 0.7 | 0.7 | 0.7 | 0.7 | 0.7 |
| (f) | Coco-Betaine | — | — | — | 3 | 3 | 3 | 2.4 |
| | Preservatives, pH Adjusters, co-solvents, fragrances, etc. | ~2 | ~2 | ~2 | ~2 | ~2 | ~2 | ~2 |
| (e) | Water | Q.S. 100 | Q.S. 100 | Q.S. 100 | Q.S. 100 | Q.S. 100 | Q.S. 100 | Q.S. 100 |

Preliminary in vitro and in vivo tests were carried out on inventive formulations to confirm whether the formulations provide desired cosmetic properties. The formulations tested showed very good properties as shown by the "✓" in the table below

| COSMETIC PROPERTY | |
|---|---|
| DISTRIBUTION | ✓ |
| FLASH FOAM | ✓ |
| FOAM ABUNDANCE | ✓ |
| CONDITIONING | ✓ |
| DETANGLING | ✓ |
| COATING (BEFORE DRYING) | ✓ |
| COATING (AFTER DRYING) | ✓ |

As shown by the table above, the inventive formulations exhibited superior distribution properties, good flash foam properties with an abundance of foam, both conditioning and detangling properties, and provided a degree of coating to the hair.

EXAMPLE 2

Evaluations

A panel of expert evaluators tested formulations B, C, D, and E, and compared these inventive compositions with a comparative, commercial benchmark, sulfate-free shampoo that is promoted for restoring moisture, body, and shine to hair, especially curly hair. The tests were carried out on the half-heads of eight individual hair models. The panel of expert evaluators assessed the technical attributes imparted to the hair of the models after shampooing the hair with the formulations. The results are presented in the table below.

"AA Hair relates" to African American hair;

"Cau, avg-course" relates to Caucasian hair that is average to course;

"His-Cau, avg-course" relates to Hispanic and Caucasian hair that is average to course;

= indicates that the result for the inventive composition was equal to the commercial benchmark;

> Indicates that the result for the inventive composition was superior to the commercial benchmark; and ≥ Indicates that the result for the inventive compositions was as good or better than the commercial benchmark.

| Technical Attributes | | | | B<br>IN8<br>AA hair | B<br>IN8<br>Cau,<br>avg-coarse | C<br>IN39<br>His-Cau,<br>avg-coarse | D<br>IN68<br>His-Cau,<br>avg-coarse | E<br>IN92<br>His-Cau,<br>avg-coarse |
|---|---|---|---|---|---|---|---|---|
| Moisturizing/Care | Detangling | Detangling | Wet hair | n/a | > | = | = | ≥ |
| | | | Dry hair | n/a | = | n/a | ≥ | ≥ |
| | Moisturized Feel | Dry Ends-Visual | Dry hair | n/a | n/a | n/a | = | = |
| | Soft, Touchable | Suppleness | While Rinsing | = | > | = | = | = |
| | | | Wet hair | = | > | = | = | = |
| | | | Dry hair | = | = | = | = | = |
| | Smooth | Smooth feel | In Foam | = | = | > | = | ≥ |
| | | | Wet hair | = | > | = | = | ≥ |
| | | | Dry hair | = | > | = | = | ≥ |
| | | Smooth look | Dry hair | = | = | = | = | ≥ |
| | | Ease of Shaping Brush | | n/a | > | n/a | ≥ | = |
| Natural Look and Feel | Feels/looks Natural | Coating | Wet hair | = | > | = | = | = |
| | | | Dry hair | = | = | = | = | ≥ |
| | Has movement | Body | | = | = | = | = | = |
| | Has bounce | Bounce | | = | = | = | = | = |
| Clean Feel | Not heavy or weighed down | Weight | Wet hair | = | = | = | = | ≥ |
| Ease of Use | Ease/Amount of Lather | Flash Foam | | = | = | = | = | = |
| | | Abundance of Foam | | = | = | = | = | = |

The results show that the inventive formulations, in all cases and in all parameters tested, performed at least as well as the commercial benchmark, and in many cases performed significantly better than the commercial benchmark. In no cases were the inventive formulations inferior to the commercial benchmark. In addition to the improved technical attributes of the inventive formulations, Example 3 (below) shows that the inventive compositions have better viscosities than the commercial benchmark.

EXAMPLE 3

Viscosity

The viscosity of the formulations tested above in Example 2 was measured by determining the number of seconds it takes to attain 90 g of material (cleansing composition) from a constant height (19.2 cm) at 25° C. using a Ford Viscosity Cup #6, through a constant area, $9\pi$ mm$^2$. The results are presented in the table below.

| Formula | Viscosity (Using Ford Viscosity Cup #6) |
|---|---|
| B (Inventive) 43172 IN8 | 99 seconds |
| C (Inventive) 43172 IN39 | 68 seconds |
| D (Inventive) 43172 IN68 | 89 seconds |
| E (Inventive) 43172 IN77 43172 IN92 | 99 seconds |
| G (Comparative) 43172 IN77 | 60 seconds |
| Commercial Benchmark Sulfate-Free Shampoo (Comparative) | 35-47 seconds |

Inventive formulations B, C, D, and E exhibited a desirable viscosity (above 60 seconds) and remained stable. Comparative formulation G, which had only one thickening agent, was not sufficiently viscous nor did it remain stable. The commercial benchmark had the lowest viscosity, even lower than comparative formulation G, which had only one thickening agent.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

"Keratinous substrates" as used herein, includes, but is not limited to keratin fibers such as hair and/or scalp on the human head.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term "treat" (and its grammatical variations) as used herein also refers to contacting keratinous substrates such as hair with the compositions of the present disclosure.

A "rinse-off" product refers to a composition such as a hair care composition that is rinsed and/or washed with water either after or during the application of the composition onto the keratinous substrate, and before drying and/or styling said keratinous substrate. At least a portion of the composition is removed from the keratinous substrate during the rinsing and/or washing.

The term "stable" as used herein means that the composition does not exhibit phase separation and/or crystallization.

"Volatile", as used herein, means having a flash point of less than about 100° C.

"Non-volatile", as used herein, means having a flash point of greater than about 100° C.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. The term "substantially free" or "essentially free" does not refer to or include the specified material when it is present in raw materials as commercially available from suppliers.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cleansing composition comprising:
   (a) at least 3 wt. % of one or more nonionic alkypolyglucoside surfactants;
   (b) 0.1 to 5 wt. % of one or more fatty esters;
   (c) 0.2 to 50 wt. % of one or more isethionate surfactants and one or more amino acid surfactants;
   (d) 0.01 to 5 wt. % of two or more thickening agents; and
   (e) water;
      wherein the cleansing composition is essentially free of ethoxylated surfactants and sulfate surfactants.

2. The cleansing composition of claim 1, wherein the one or more nonionic alkypolyglucoside surfactants are selected from the group consisting of decyl glucoside, stearyl glucoside, lauryl glucoside, coco-glucoside, cetearyl glucoside, decyl lauryl glucoside, and mixtures thereof.

3. The cleansing composition of claim 1, wherein the one or more fatty esters of (b) are selected from the group consisting of one or more glycerol fatty esters, one or more sucrose fatty esters, one or more sorbitan fatty esters, one or more fatty alcohol esters, and mixtures thereof.

4. The cleansing composition of claim 3, comprising one or more glycerol fatty esters.

5. The cleansing composition of claim 1 comprising one or more glycerol fatty esters selected from the group consisting of glyceryl caprate, glyceryl caprylate, glyceryl oleate, glyceryl linoleate, glyceryl myristate, glyceryl capromyristate, glyceryl stearate, glyceryl hydroxy stearate, glyceryl isostearate, glyceryl ricinoleate, glyceryl dilaurate, glyceryl dioleate, glyceryldistearate, glycerylmono/dicaprylate, glycerylmono/dimyristate, glycerylstearatepalmitate, glyceryltricaprate/caprylate, caprylic/capricdiglycerylsuccinate, caprylic/capric glycerides, caprylic/capric/isostearic/adipictriglycerides, caprylic/capric/linoleictriglycerides, caprylic/caprictriglycerides, caprylic/capric/stearictriglycerides, glyceryltrilaurate/stearate, glyceryldi/tripalmitostearate, glyceryldi/tritristearate, caprylictriglyceride, caprylic/capric/laurictriglycerides, glyceryltriheptanoate, glyceryl trioctanoate, glyceryl trilaurate, glyceryl trioleate, glyceryltristearate, glyceryltris-12-hydroxystearate, glyceryltriacetyl hydroxystearate, glyceryl triacetyl ricinioleate, glyceryl triisostearate, glyceryl tribehenate, and mixtures thereof.

6. The cleansing composition of claim 3, comprising one or more sucrose fatty esters.

7. The cleansing composition of claim 6 comprising one or more sucrose fatty esters selected from the group consisting of sucrose cocoate, sucrose laurate, sucrose myristate, sucrose palmitate, sucrose polystearate, sucrose tristearate, sucrose distearate, sucrose stearate, sucrose dilaurate, sucrose hexaerucate, sucrose oleate, sucrose pentaerucate, sucrose polybehenate, sucrose polycottonseedate, sucrose polylaurate, sucrose polylinoleate, sucrose polypalmate, sucrose polyoleate, sucrose polysoyate, sucrose ricinoleate, sucrose tetraisostearate, sucrose tribehenate, sucrose hexaoleate/hexapalmitate/hexastearate, sucrose hexapalmitate, sucrose trilaurate, and mixtures thereof.

8. The cleansing composition of claim 1 comprising one or more isethionate surfactants selected from the group consisting of sodium cocoyl isethionate, sodium lauroyl isethionate, sodium oleoyl isethionate, sodium oleoyl methyl isethionate, sodium lauroyl methyl isethionate, sodium stearoyl isethionate, sodium stearoyl methyl isethionate, ammonium cocoyl isethionate, and mixtures thereof.

9. The cleansing composition of claim 1 comprising one or more amino acid surfactants selected from the group consisting of taurates, alanine or alaninate surfactants, sarcosinate surfactants, aspartate surfactants, and mixtures thereof.

10. The cleansing composition of claim 9 comprising one or more sarcosinate surfactants.

11. The cleansing composition of claim 10 comprising one or more sarcosinate surfactants selected from the group consisting of potassium lauroyl sarcosinate, potassium cocoyl sarcosinate, sodium cocoyl sarcosinate, sodium lauroyl sarcosinate, sodium myristoyl sarcosinate, and sodium palmitoyl sarcosinate, and mixtures thereof.

12. The cleansing composition of claim 1 comprising two or more thickening agents selected from the group consisting of carboxylic acid polymers, crosslinked polyacrylate polymer(s), polyacrylamide polymers, polysaccharides, and gums.

13. The cleansing composition of claim 12 comprising one or more gums selected from the group consisting of acacia, agar, algin, alginic acid, ammonium alginate, amylopectin, calcium alginate, calcium carrageenan, carrageenan, dextrin, gelatin, gellan gum, guar gum, hydroxypropyl guar, guar hydroxypropyltrimonium chloride, hydroxypropyl guar hydroxypropyltrimonium chloride, karaya gum, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

14. A method for washing a body or hair comprising applying a cleansing composition according to claim 1 to the body or hair, and optionally rinsing the cleansing composition from the body.

15. The cleansing composition of claim 1, wherein the cleansing composition is essentially free of silicone oils.

16. A cleansing composition comprising:
   (a) about 3 to 25 wt. % one or more nonionic alkypolyglucoside surfactants selected from decyl glucoside, stearyl glucoside, lauryl glucoside, coco-glucoside, cetearyl glucoside, decyl lauryl glucoside, and mixtures thereof;
   (b) about 0.1 to about 5 wt. % of one or more glycerol fatty esters;
   (c) about 0.2 to about 20 wt. % of one or more isethionate surfactants and one or more sarcosinate surfactants;
   (d) about 0.01 to about 5 wt. % of two or more thickening gums;
   (e) about 50 to 90 wt. % water; and
   (f) optionally, one or more amphoteric surfactants;
      wherein all percentages are based on the total weight of the cleansing composition and the cleansing composition is essentially free of ethoxylated surfactants and sulfate surfactants.

17. The cleansing composition of claim 16 comprising one or more glycerol fatty esters selected from glyceryl caprate, glyceryl caprylate, glyceryl oleate, glyceryl linoleate, glyceryl myristate, glyceryl capromyristate, glyceryl stearate, glyceryl hydroxy stearate, glyceryl isostearate, glyceryl ricinoleate, glyceryl dilaurate, glyceryl dioleate, glyceryldistearate, glycerylmono/dicaprylate, glycerylmono/dimyristate, glycerylstearatepalmitate, glyceryltricaprate/caprylate, caprylic/capricdiglycerylsuccinate, caprylic/capric glycerides, caprylic/capric/isostearic/adipictriglycerides, caprylic/capric/linoleictriglycerides, caprylic/ caprictriglycerides, caprylic/capric/stearictriglycerides, glyceryltrilaurate/stearate, glyceryldi/tripalmitostearate, glyceryldi/tritristearate, caprylictriglyceride, caprylic/capric/laurictriglycerides, glyceryltriheptanoate, glyceryl trioctanoate, glyceryl trilaurate, glyceryl trioleate, glyceryltristearate, glyceryltris-12-hydroxystearate, glyceryltriacetyl hydroxystearate, glyceryl triacetyl ricinioleate, glyceryl triisostearate, glyceryl tribehenate, and mixtures thereof.

18. The cleansing composition of claim 16 comprising one or more isethionate surfactants selected from the group consisting of sodium cocoyl isethionate, sodium lauroyl isethionate, sodium oleoyl isethionate, sodium oleoyl methyl isethionate, sodium lauroyl methyl isethionate, sodium stearoyl isethionate, sodium stearoyl methyl isethionate, ammonium cocoyl isethionate, and mixtures thereof.

19. The cleansing composition of claim 16 comprising one or more sarcosinate surfactants selected from the group consisting of potassium lauroyl sarcosinate, potassium cocoyl sarcosinate, sodium cocoyl sarcosinate, sodium lauroyl sarcosinate, sodium myristoyl sarcosinate, and sodium palmitoyl sarcosinate, and mixtures thereof.

20. The cleansing composition of claim 1, wherein the cleansing composition is essentially free of silicone oils.

21. A method for washing a body or hair comprising applying a cleansing composition according to claim 16 to the body or hair, and optionally rinsing the cleansing composition from the body.

* * * * *